(12) United States Patent
Kamen et al.

(10) Patent No.: US 12,403,252 B2
(45) Date of Patent: Sep. 2, 2025

(54) INFUSION DEVICE SYSTEM AND APPARATUS

(71) Applicant: DEKA Products Limited Partnership, Manchester, NH (US)

(72) Inventors: Dean Kamen, Bedford, NH (US); Kevin L. Grant, Litchfield, NH (US)

(73) Assignee: DEKA PRODUCTS LIMITED PARTNERSHIP, Manchester, NH (US)

( * ) Notice: Subject to any disclaimer, the term of this patent is extended or adjusted under 35 U.S.C. 154(b) by 414 days.

(21) Appl. No.: 17/878,217

(22) Filed: Aug. 1, 2022

(65) Prior Publication Data

US 2022/0362459 A1 Nov. 17, 2022

Related U.S. Application Data

(63) Continuation of application No. 16/572,032, filed on Sep. 16, 2019, now Pat. No. 11,400,209, which is a
(Continued)

(51) Int. Cl.
*A61M 5/162* (2006.01)
*A61M 5/14* (2006.01)
(Continued)

(52) U.S. Cl.
CPC .......... *A61M 5/162* (2013.01); *A61M 5/1413* (2013.01); *A61M 5/14248* (2013.01); *A61M 5/158* (2013.01); *A61M 2005/14268* (2013.01); *A61M 2005/1585* (2013.01); *A61M 2005/1588* (2013.01); *A61M 2205/0266* (2013.01); *A61M 2205/3337* (2013.01); *A61M 2205/3379* (2013.01); *A61M 2205/3389* (2013.01);
(Continued)

(58) Field of Classification Search
None
See application file for complete search history.

(56) References Cited

U.S. PATENT DOCUMENTS

| 4,755,173 A | * | 7/1988 | Konopka | A61M 25/0606 604/122 |
| 6,685,674 B2 | | 2/2004 | Douglas et al. | |

(Continued)

FOREIGN PATENT DOCUMENTS

| WO | WO/2009/016638 A1 | 2/2009 |
| WO | WO/2009/125398 A2 | 10/2009 |
| WO | WO/2010/113159 A1 | 10/2010 |

OTHER PUBLICATIONS

International Preliminary Report on Patentability for International Application No. PCT/US2016/013603 dated Jul. 18, 2017.
(Continued)

*Primary Examiner* — Manuel A Mendez
(74) *Attorney, Agent, or Firm* — McCormick, Paulding & Huber PLLC

(57) ABSTRACT

An infusion device. The infusion device includes a top portion comprising an introduction needle, and a bottom portion comprising a cannula, the top portion removably attached to the bottom portion, wherein the introduction needle is used to insert the cannula, and wherein after insertion, the top portion is removed from the bottom portion.

15 Claims, 37 Drawing Sheets

Related U.S. Application Data continuation of application No. 14/996,559, filed on Jan. 15, 2016, now Pat. No. 10,413,661.

(60) Provisional application No. 62/103,841, filed on Jan. 15, 2015.

(51) Int. Cl.
  *A61M 5/142* (2006.01)
  *A61M 5/158* (2006.01)

(52) U.S. Cl.
  CPC ... *A61M 2205/36* (2013.01); *A61M 2205/582* (2013.01); *A61M 2205/8206* (2013.01)

(56) References Cited

U.S. PATENT DOCUMENTS

| | | | |
|---|---|---|---|
| 8,083,730 B2 | 12/2011 | Miesel | |
| 8,303,549 B2* | 11/2012 | Mejlhede | A61M 5/14248 604/200 |
| 10,413,661 B2 | 9/2019 | Kamen et al. | |

OTHER PUBLICATIONS

International Search Report for International Application No. PCT/US2016/013603 dated Jul. 4, 2017.
Written Opinion of the International Searching Authority for International Application No. PCT/US2016/013603 dated Jul. 4, 2017.

* cited by examiner

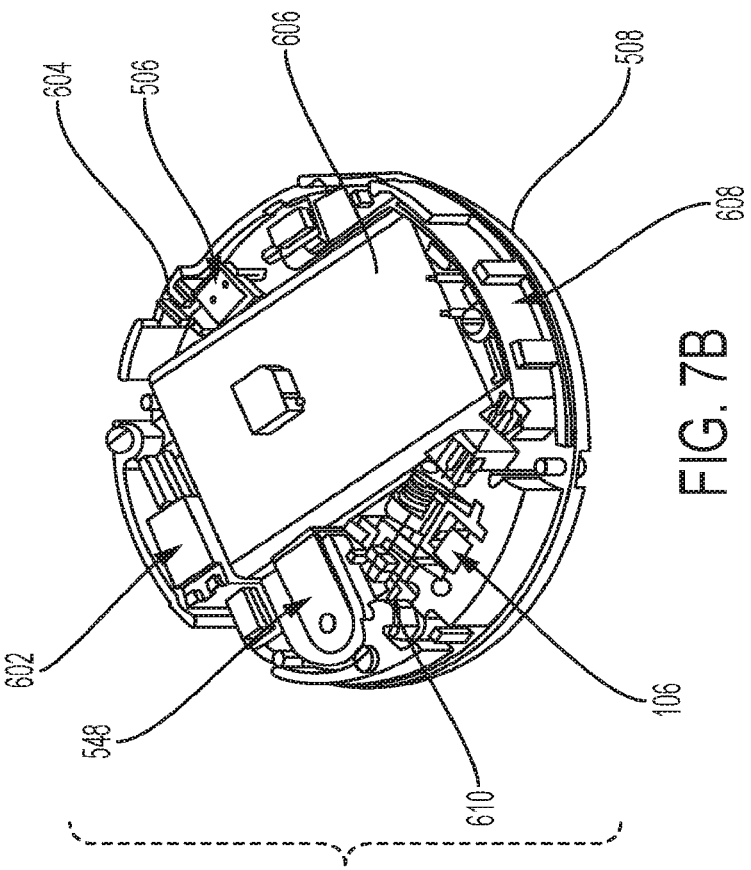
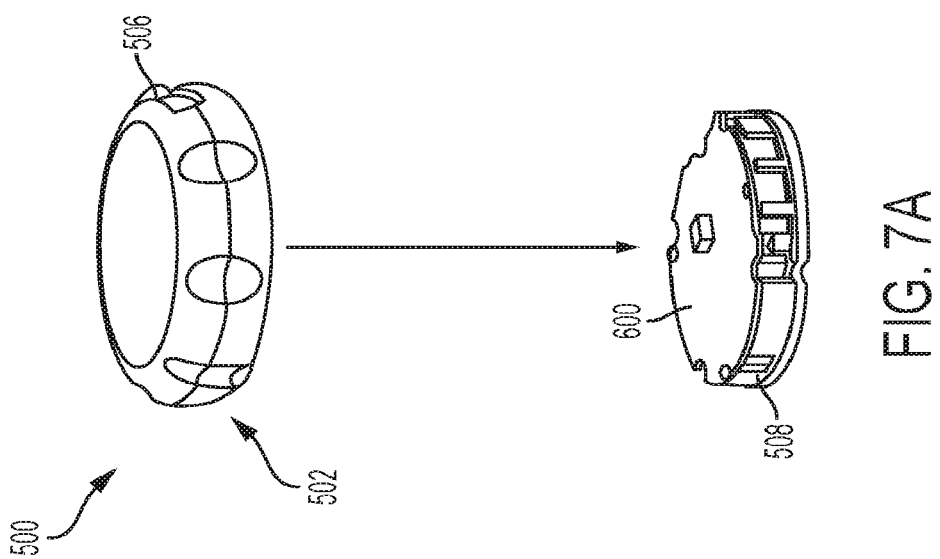
FIG. 7B
FIG. 7A

INFUSION DEVICE SYSTEM AND APPARATUS

CROSS REFERENCE TO RELATED APPLICATION(S)

The present application is a continuation of U.S. patent application Ser. No. 16/572,032, filed Sep. 16, 2019, which is a continuation of U.S. patent application Ser. No. 14/996,559, filed Jan. 15, 2016, now U.S. Pat. No. 10,413,661, issued Sep. 17, 2019 and entitled Apparatus, System and Method for Fluid Delivery which is a Non-provisional Application which claims priority from U.S. Provisional Patent Application Ser. No. 62/103,841, filed Jan. 15, 2015 and entitled Infusion Pump Assembly, which is hereby incorporated herein by reference in its entirety.

FIELD OF THE INVENTION

This application relates generally to fluid delivery systems, and more particularly to an infusion pump assemblies and infusion devices, systems and apparatus.

BACKGROUND

Many potentially valuable medicines or compounds, including biologicals, are not orally active due to poor absorption, hepatic metabolism or other pharmacokinetic factors. Additionally, some therapeutic compounds, although they can be orally absorbed, are sometimes required to be administered so often it is difficult for a patient to maintain the desired schedule. In these cases, parenteral delivery is often employed or could be employed.

Effective parenteral routes of drug delivery, as well as other fluids and compounds, such as subcutaneous injection, intramuscular injection, and intravenous (IV) administration include puncture of the skin with a needle or stylet. Insulin is an example of a therapeutic fluid that is self-injected by millions of diabetic patients. Users of parenterally delivered drugs may benefit from a wearable device that would automatically deliver needed drugs/compounds over a period of time.

To this end, there have been efforts to design portable and wearable devices for the controlled release of therapeutics. Such devices are known to have a reservoir such as a cartridge, syringe, or bag, and to be electronically controlled. These devices suffer from a number of drawbacks including the malfunction rate. Reducing the size, weight and cost of these devices is also an ongoing challenge. Additionally, these devices often apply to the skin and pose the challenge of frequent re-location for application.

SUMMARY OF THE INVENTION

In accordance with first implementation, an infusion device system is disclosed. The infusion device system includes a disposable housing assembly comprising an infusion device mating assembly attached to the disposable housing assembly comprising a piercing needle and a reservoir, wherein the piercing needle fluidly connected to the reservoir; and an infusion device including a top portion comprising an introduction needle and a bottom portion including a septum and a cannula, the top portion removably attached to the bottom portion. Wherein the introduction needle is used to insert the cannula, and wherein after insertion, the top portion is removed from the bottom portion, wherein the infusion device mating assembly configured to attach to the bottom portion of the infusion device, wherein the piercing needle configured to pierce the septum, and wherein when the infusion device mating assembly is attached to the bottom portion of the infusion device, the cannula is fluidly connected to the reservoir.

Some embodiments of this implementation include one or more of the following. Wherein the system further includes a predetermined length of tubing comprising a first end and a second end. Wherein the first end of the tubing configured to attach to the bottom portion of the infusion device and the second end of the tubing configured to attach to the infusion device mating assembly. Wherein the second end of the tubing configured to attach to the piercing needle, wherein the tubing is fluidly connected to the reservoir. Wherein the system further includes an autoinserter. Wherein the system further includes a reusable housing assembly configured to removably attach to the disposable housing assembly. Wherein the reusable housing assembly includes a volume sensor assembly. Wherein the disposable housing assembly includes a pumping chamber.

In accordance with another implementation, an infusion device system is disclosed. The infusion device system includes a disposable housing assembly including an infusion device mating assembly attached to the disposable housing assembly comprising a piercing needle and a reservoir, wherein the piercing needle fluidly connected to the reservoir. The system also includes a resusable housing assembly configured to removably attach to the disposable housing assembly and an infusion device. The infusion device includes a top portion including an introduction needle and a bottom portion including a septum and a cannula, the top portion removably attached to the bottom portion. Wherein the introduction needle is used to insert the cannula, and wherein after insertion, the top portion is removed from the bottom portion, wherein the infusion device mating assembly configured to attach to the bottom portion of the infusion device, wherein the piercing needle configured to pierce the septum, and wherein when the infusion device mating assembly is attached to the bottom portion of the infusion device, the cannula is fluidly connected to the reservoir.

Some embodiments of this implementation include one or more of the following. Wherein the infusion device system further includes a predetermined length of tubing including a first end and a second end. Wherein the first end of the tubing configured to attach to the bottom portion of the infusion device and the second end of the tubing configured to attach to the infusion device mating assembly. Wherein the second end of the tubing configured to attach to the piercing needle, wherein the tubing is fluidly connected to the reservoir. Wherein the system further including an autoinserter. Wherein the reusable housing assembly including a volume sensor assembly. Wherein the disposable housing assembly including a pumping chamber.

In accordance with first implementation, an infusion device is disclosed. The infusion device includes a top portion including an introduction needle and a bottom portion comprising a septum and a cannula, the top portion removably attached to the bottom portion, wherein the introduction needle is used to insert the cannula, and wherein after insertion, the top portion is removed from the bottom portion, wherein the bottom portion configured to attach to an infusion device mating assembly of an infusion pump assembly, wherein when the infusion device mating assembly is attached to the bottom portion of the infusion device, the cannula is fluidly connected to a reservoir.

Some embodiments of this implementation include one or more of the following. The infusion device further including a predetermined length of tubing comprising a first end and a second end. Wherein the first end of the tubing configured to attach to the bottom portion of the infusion device and the second end of the tubing configured to attach to the infusion device mating assembly. The infusion device further including an autoinserter. Wherein the bottom portion including a septum.

The details of one or more embodiments are set forth in the accompanying drawings and the description below. Other features and advantages will become apparent from the description, the drawings, and the claims.

BRIEF DESCRIPTION OF THE DRAWINGS

FIG. 7A is an exploded view of various components of an infusion pump assembly;

FIG. 7B is an isometric view of a portion of the infusion pump assembly;

Like reference symbols in the various drawings indicate like elements.

DETAILED DESCRIPTION

Figure 1A:
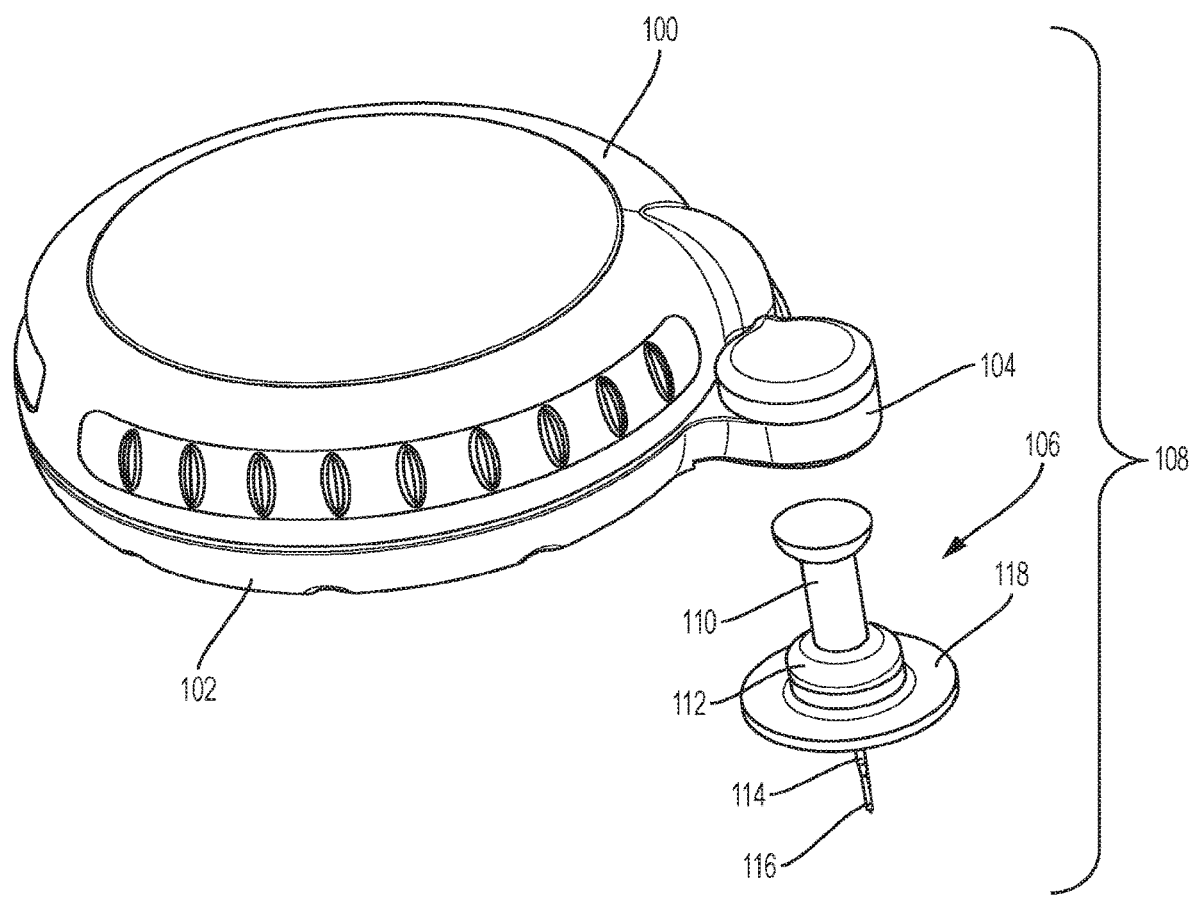
FIGS. 1A-3C are various views of one embodiment of an infusion device system.
Figure 1B:
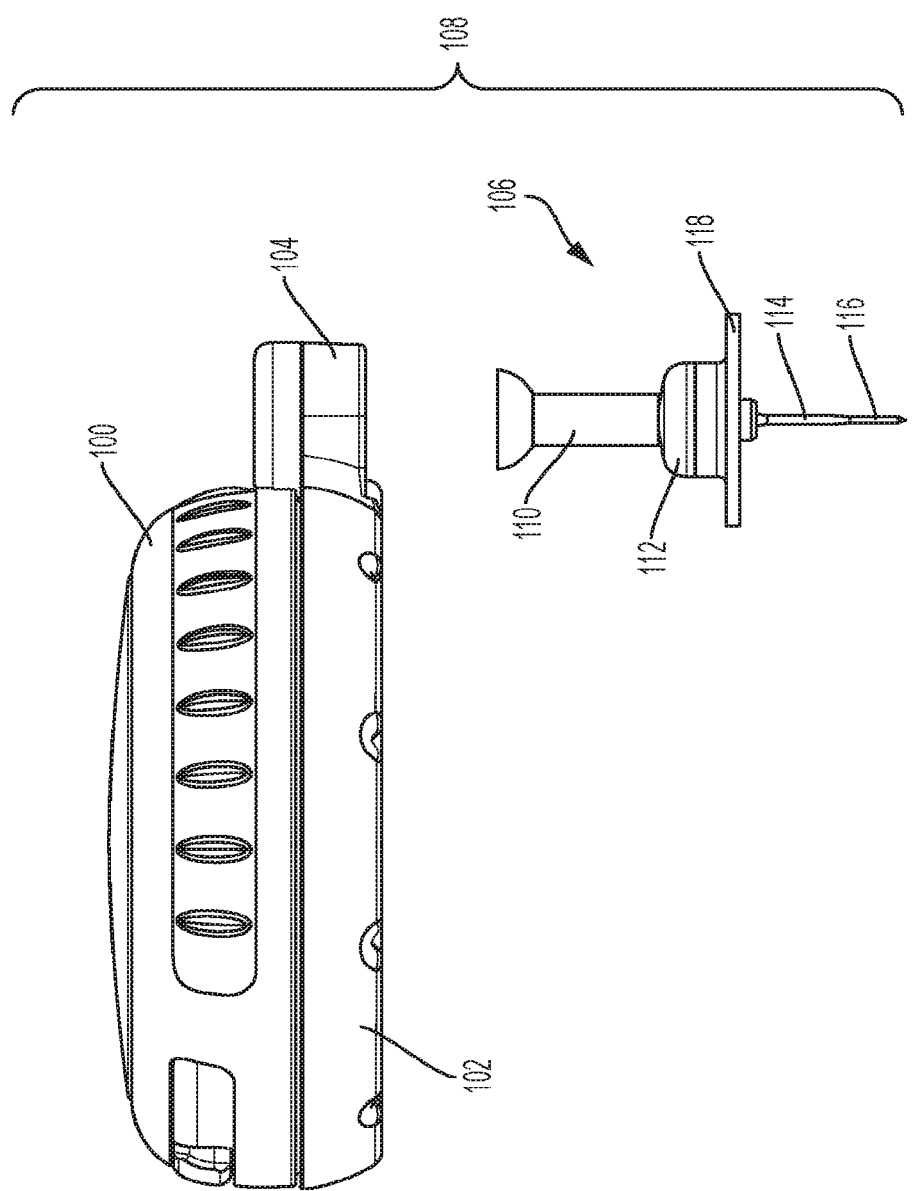
Figure 1C:
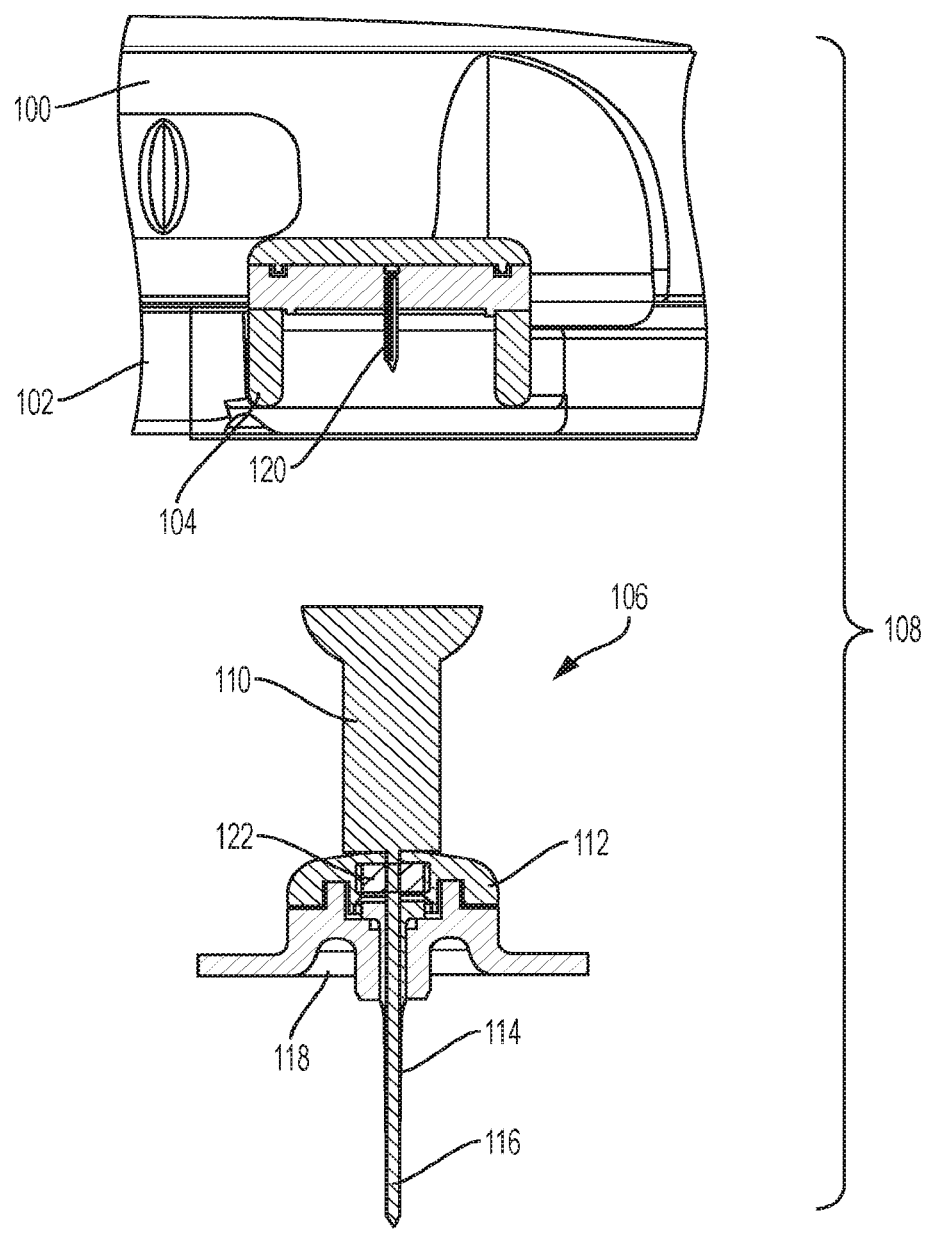
Figure 2A:
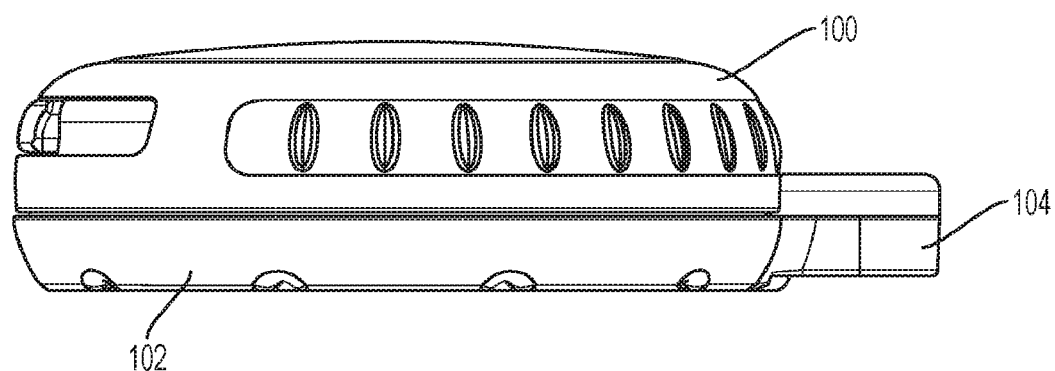
Figure 2B:
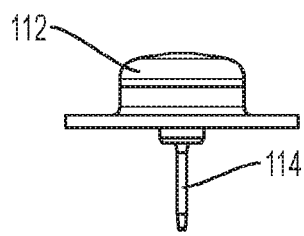
Figure 2C:
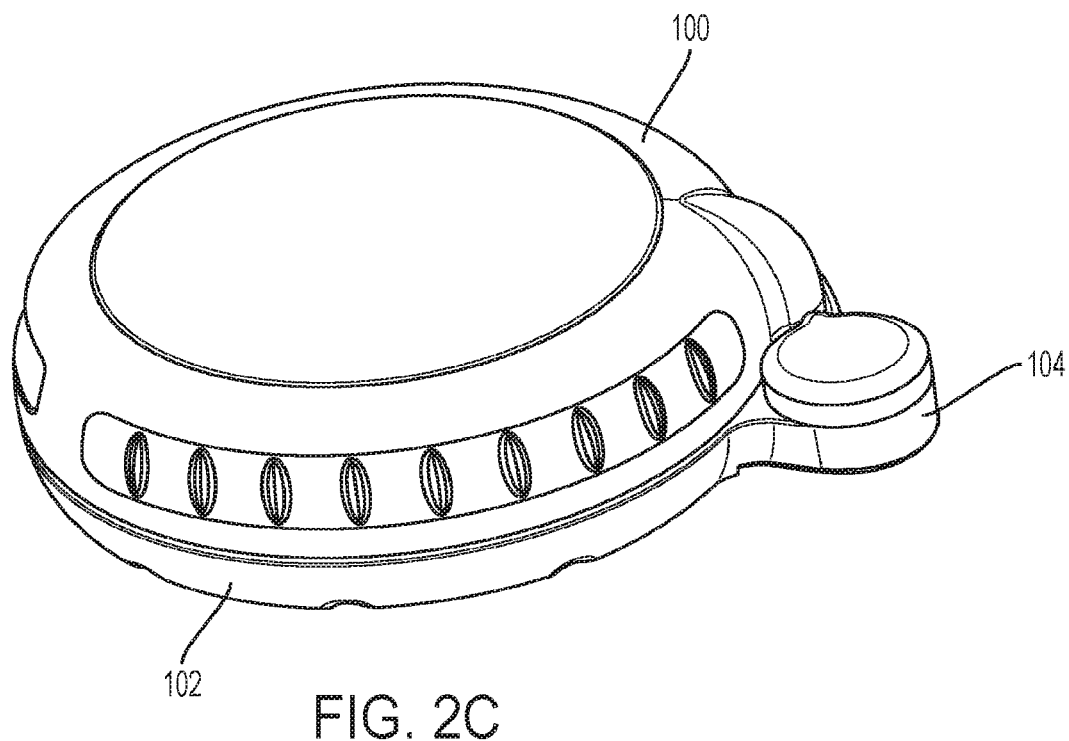
Figure 2D:
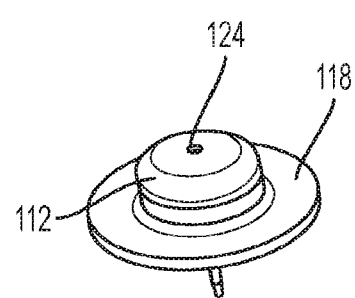
Figure 2E:
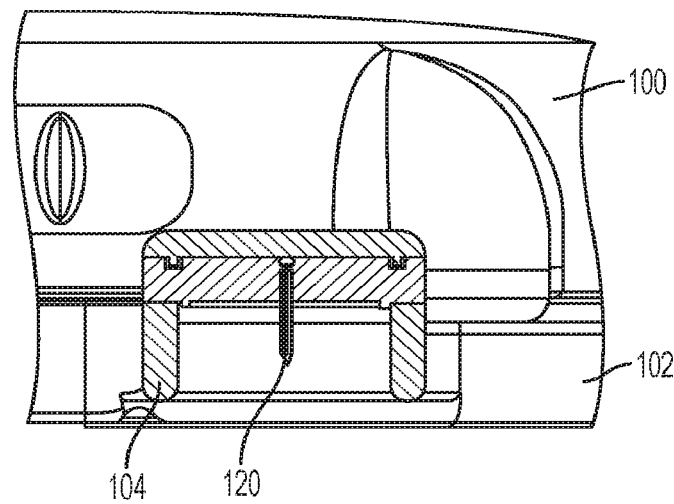
Figure 2F:
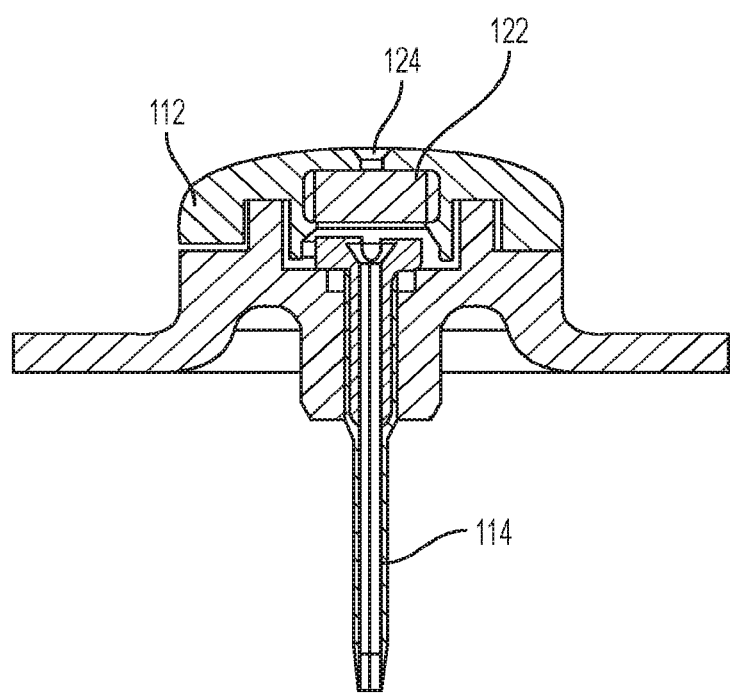
Figure 3A:
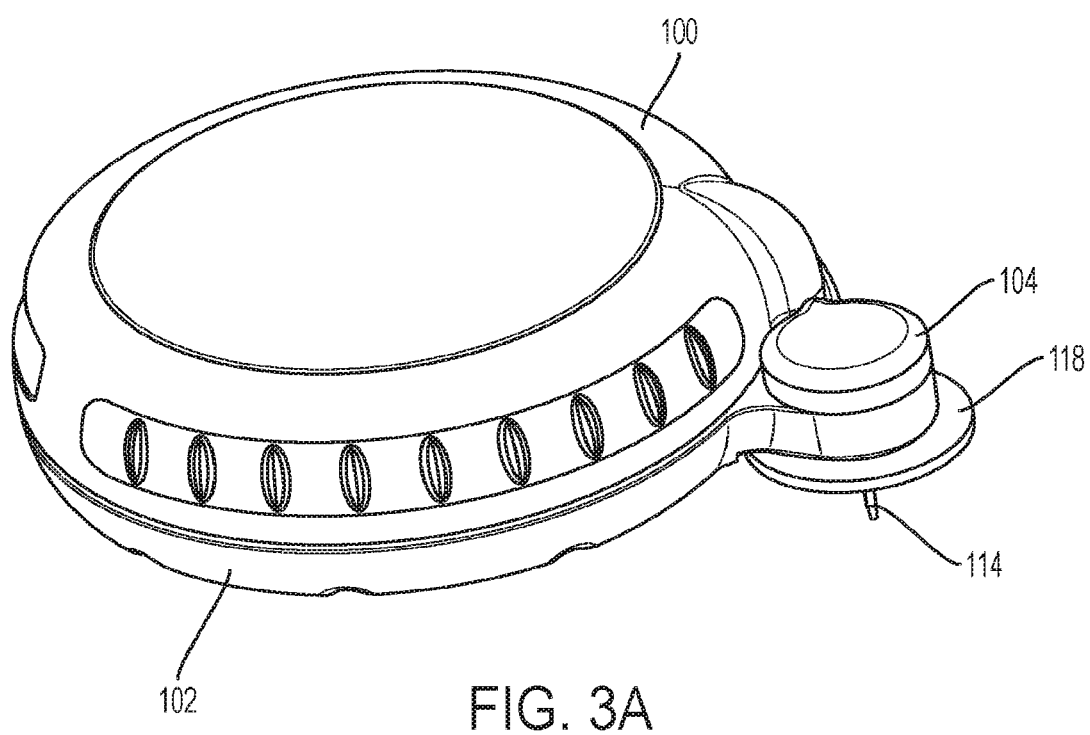
Figure 3B:
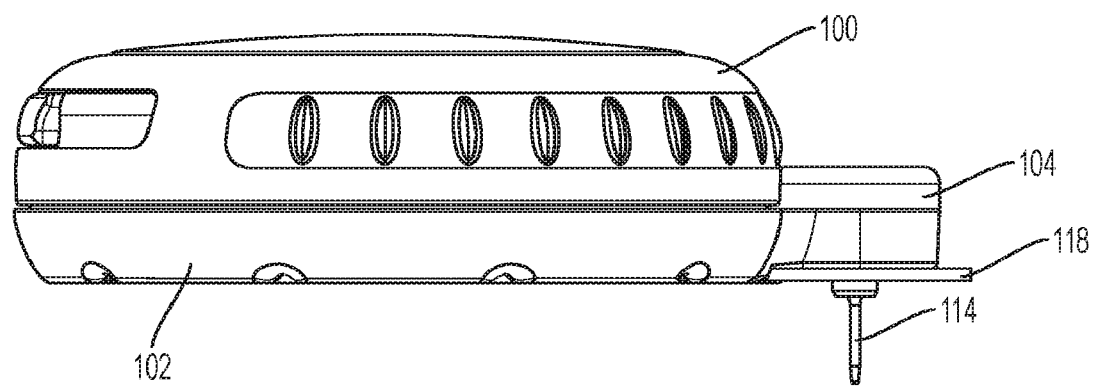
Figure 3C:
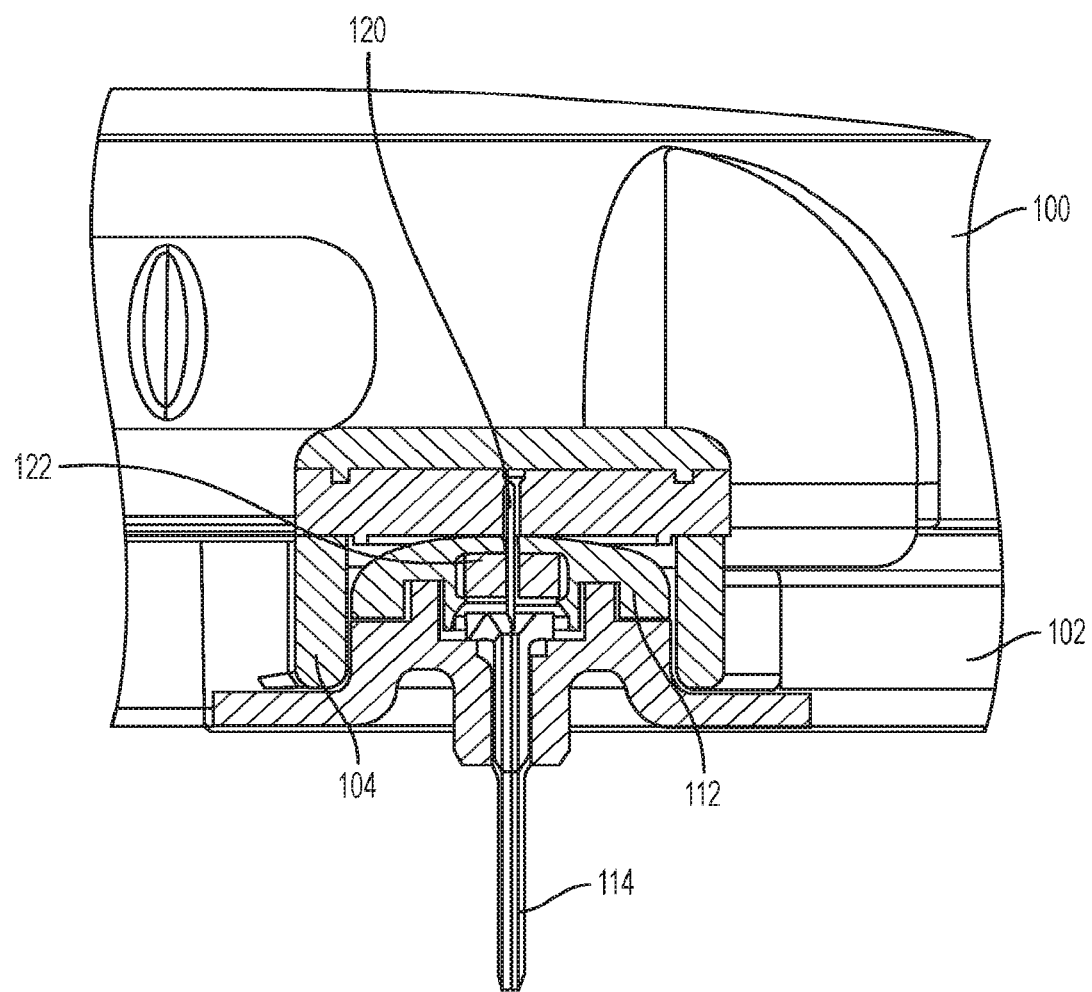
Figure 4A:
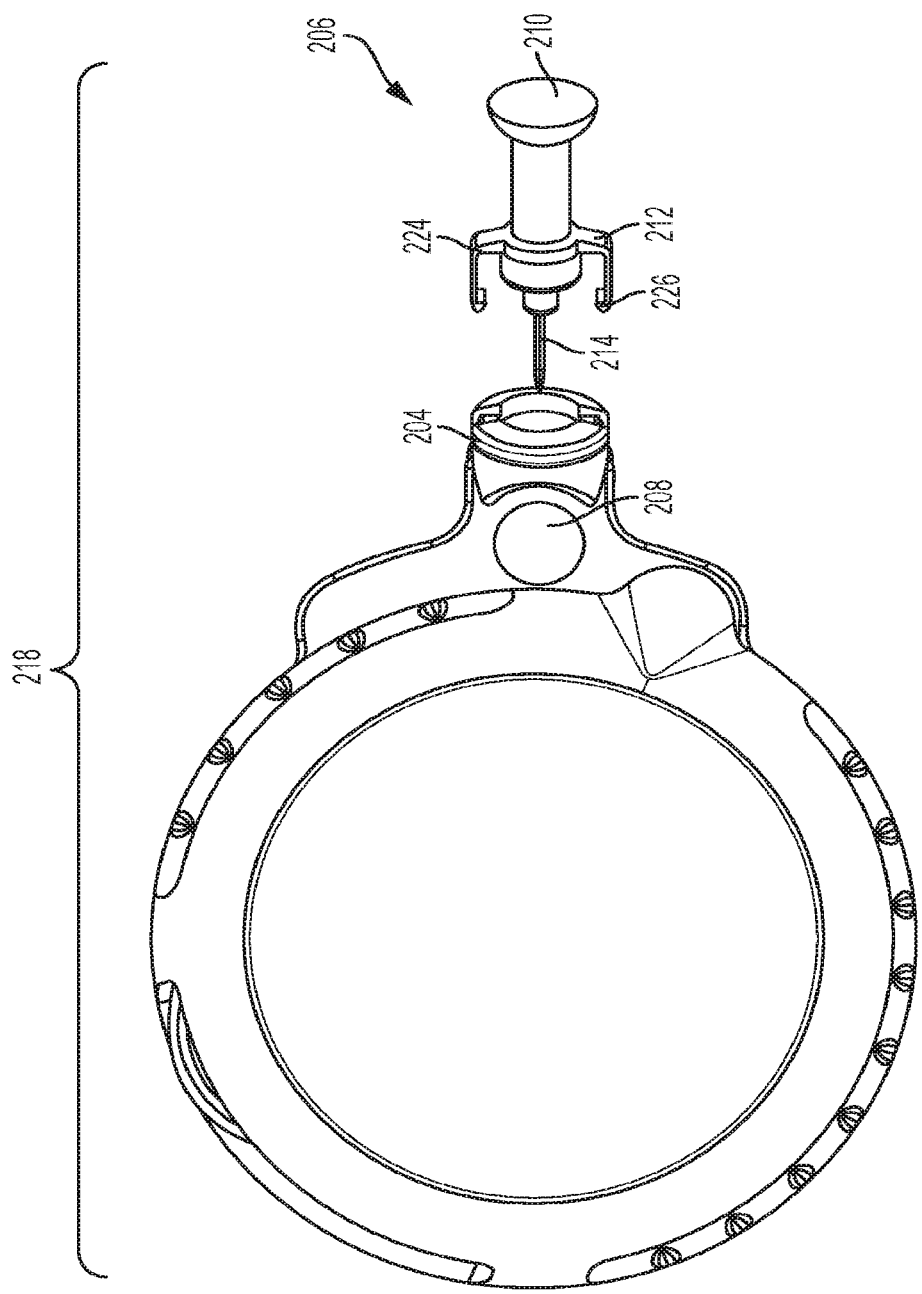
FIGS. 4A-4K are various views of one embodiment of an infusion device system.
Figure 4B:
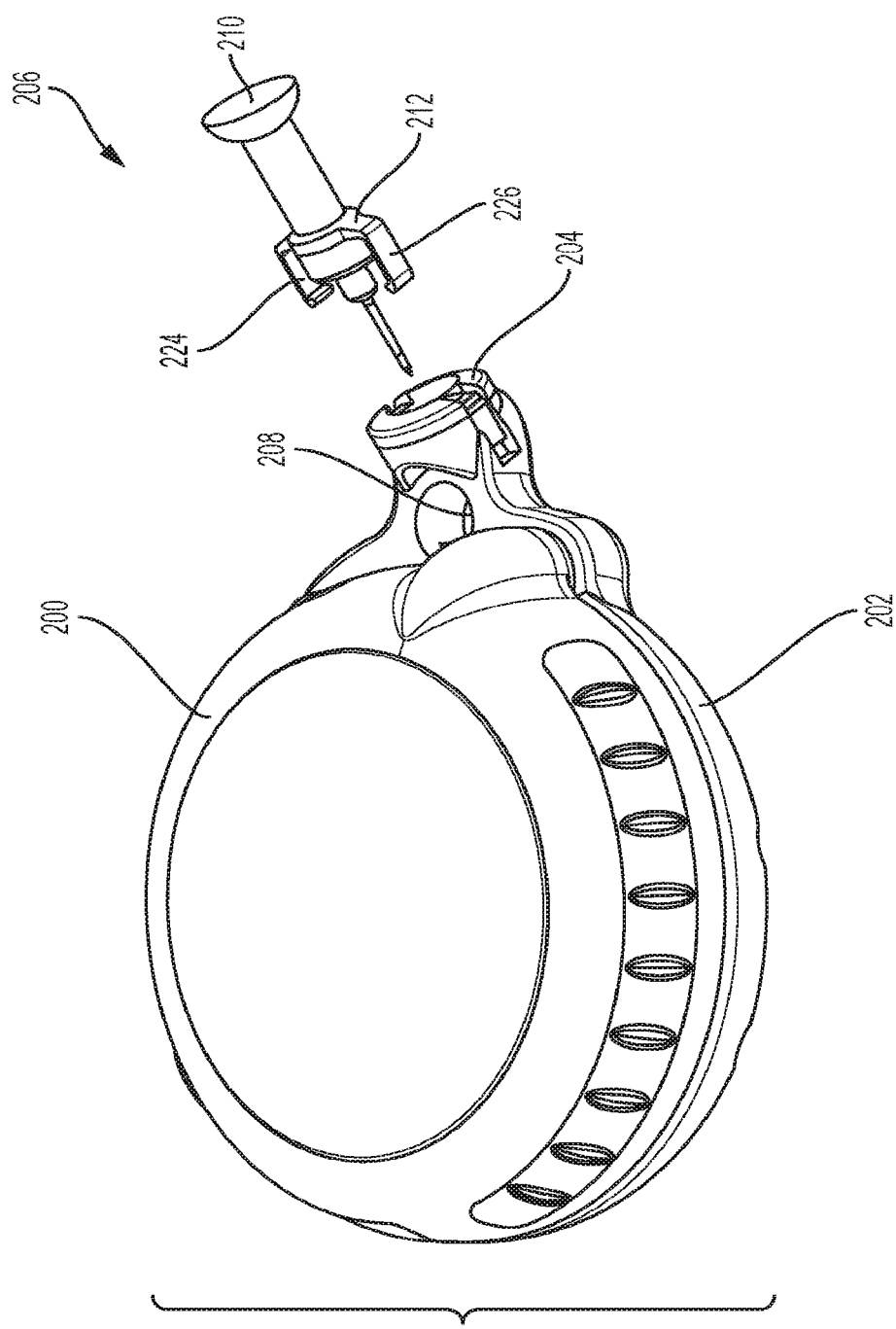
Figure 4C:
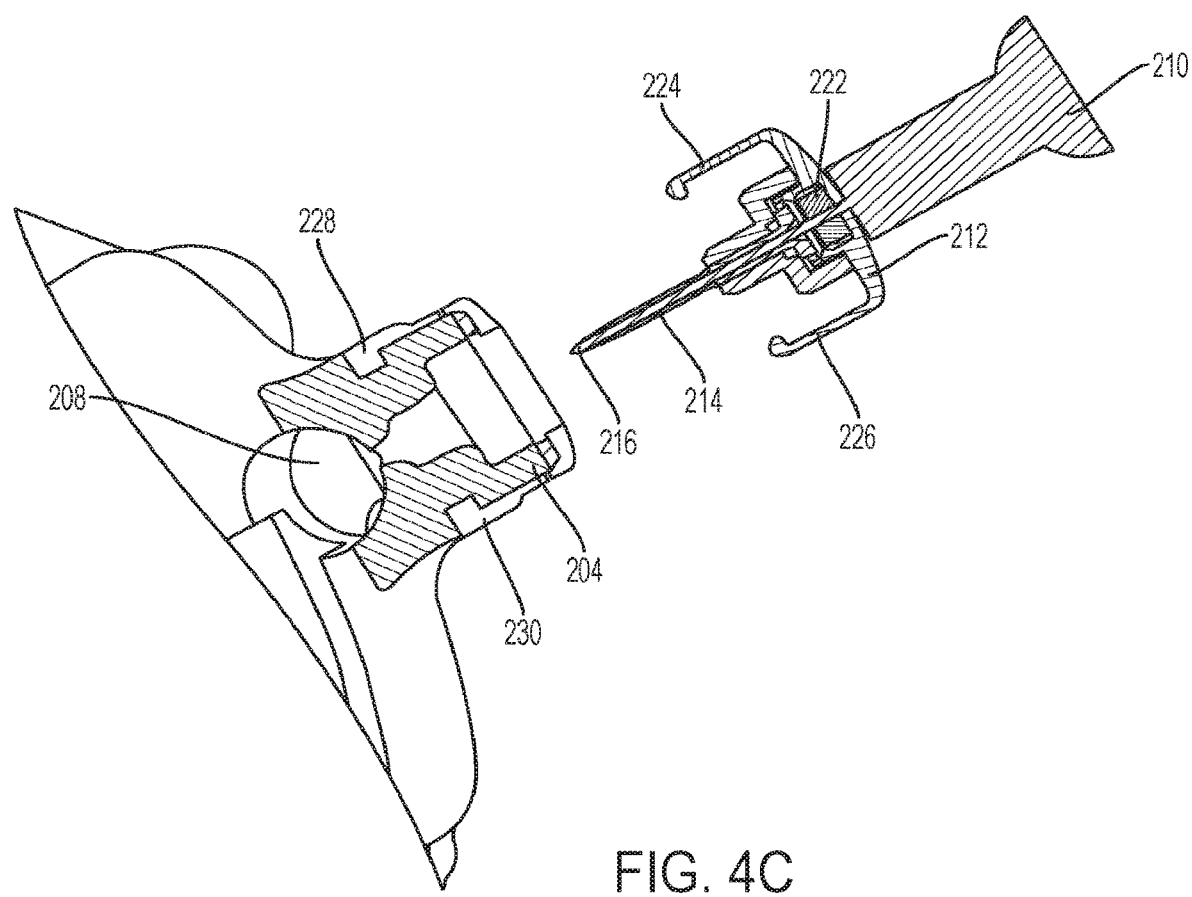
Figure 4D:
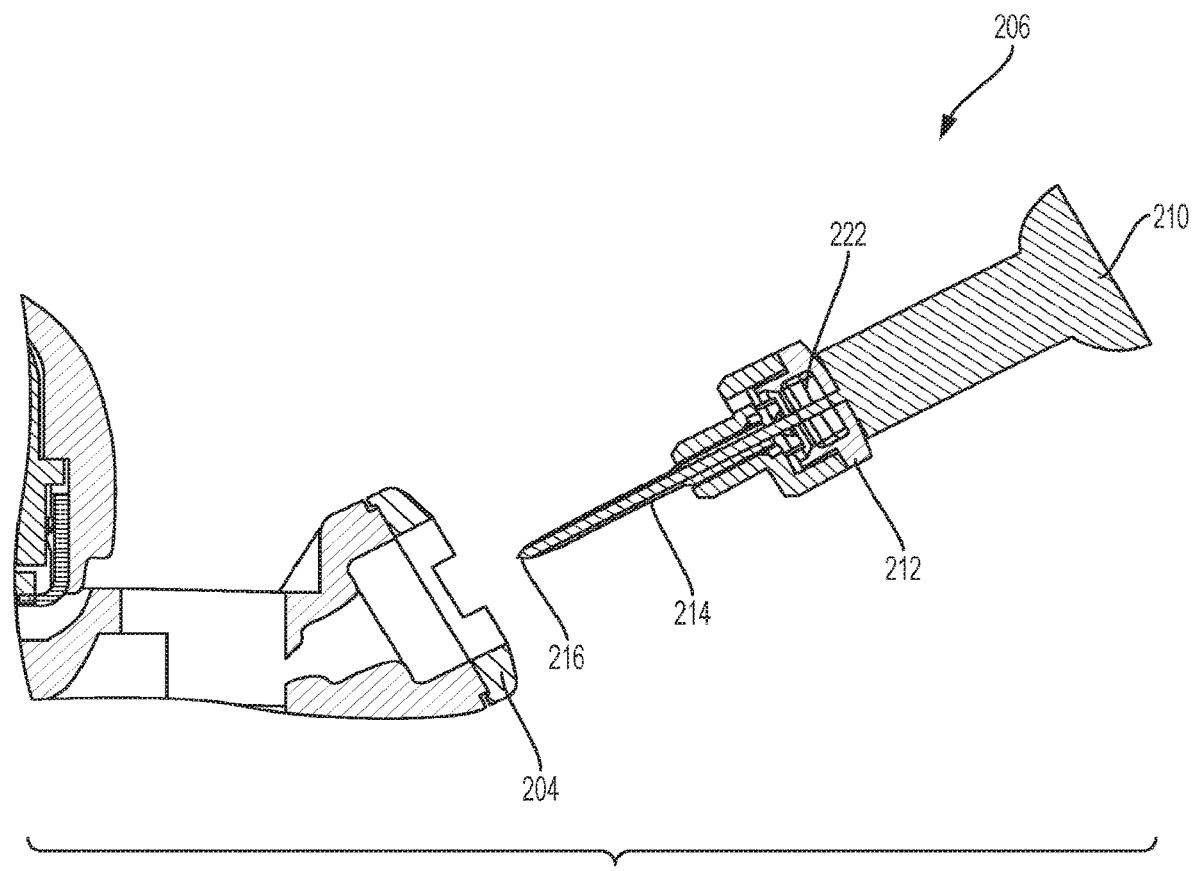
Figure 4E:
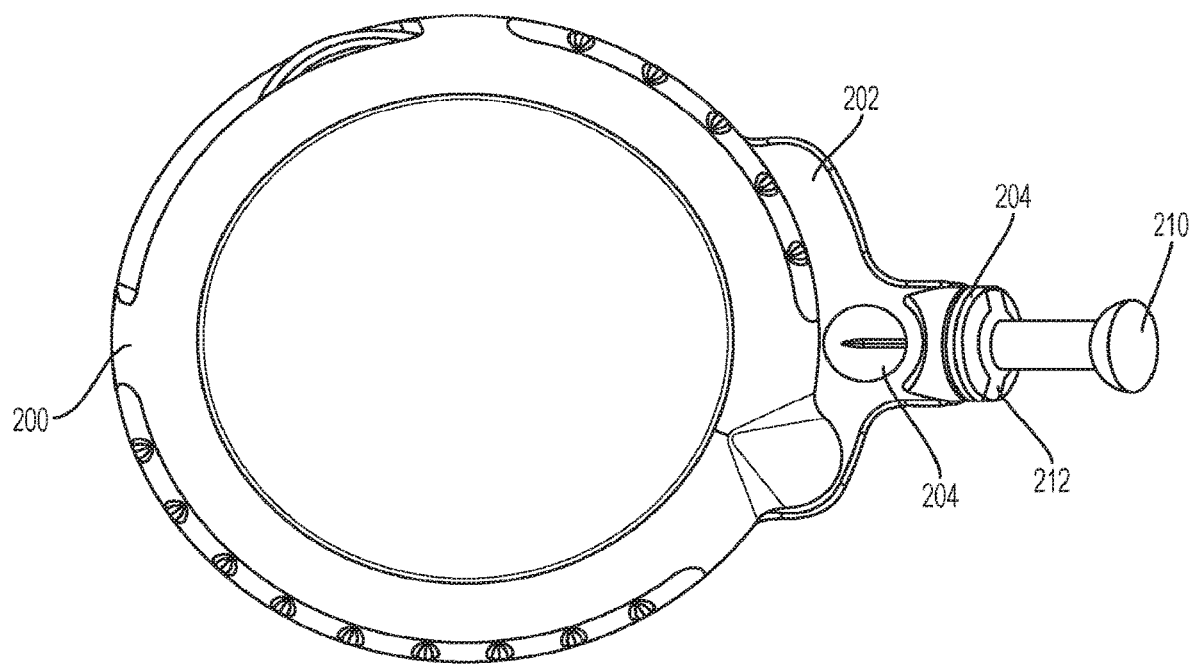
Figure 4F:
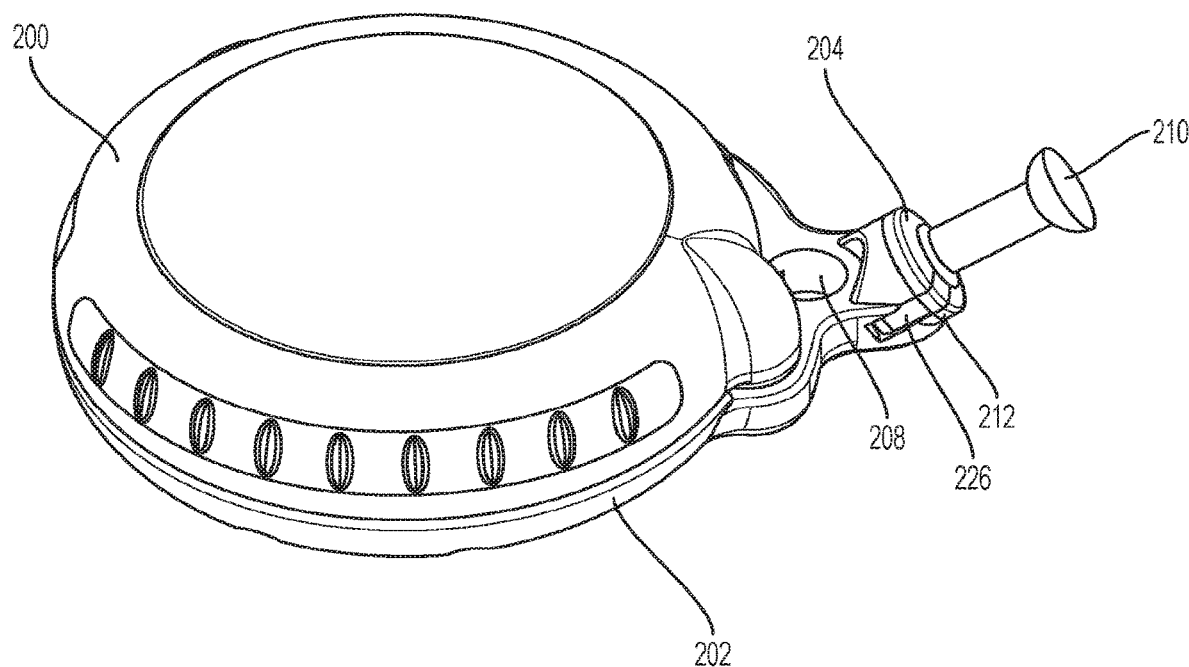
Figure 4G:
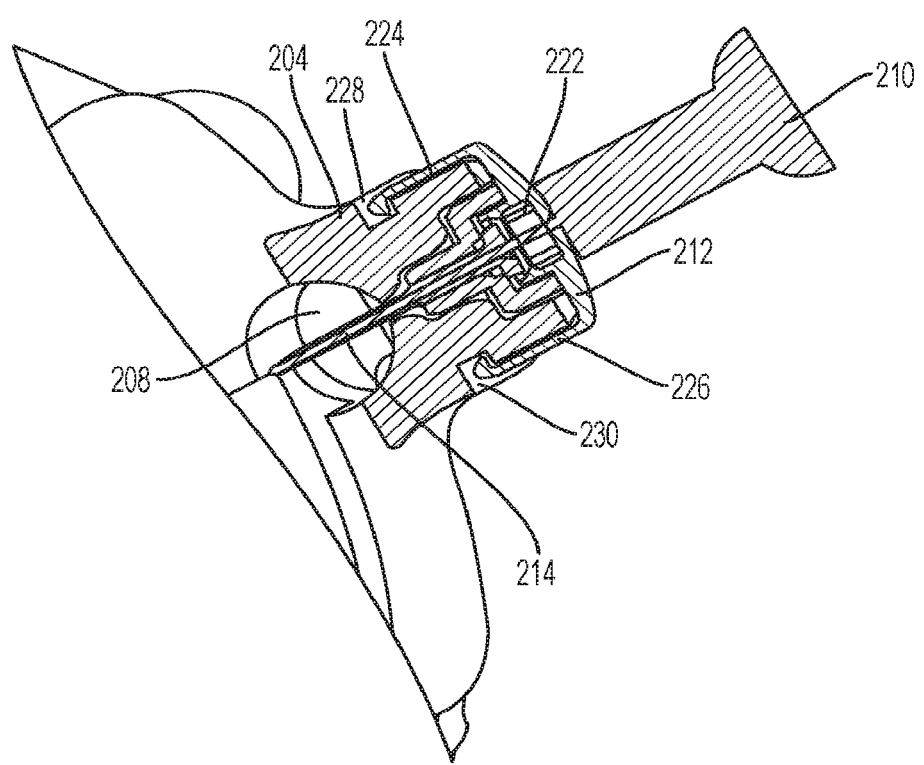
Figure 4H:
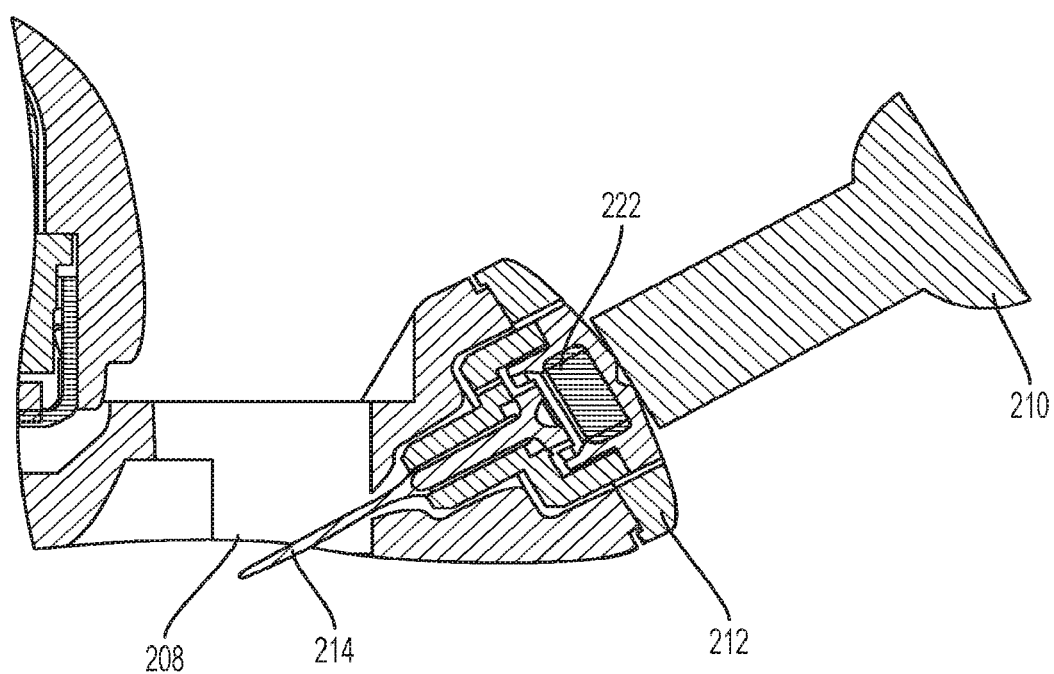
Figure 4I:
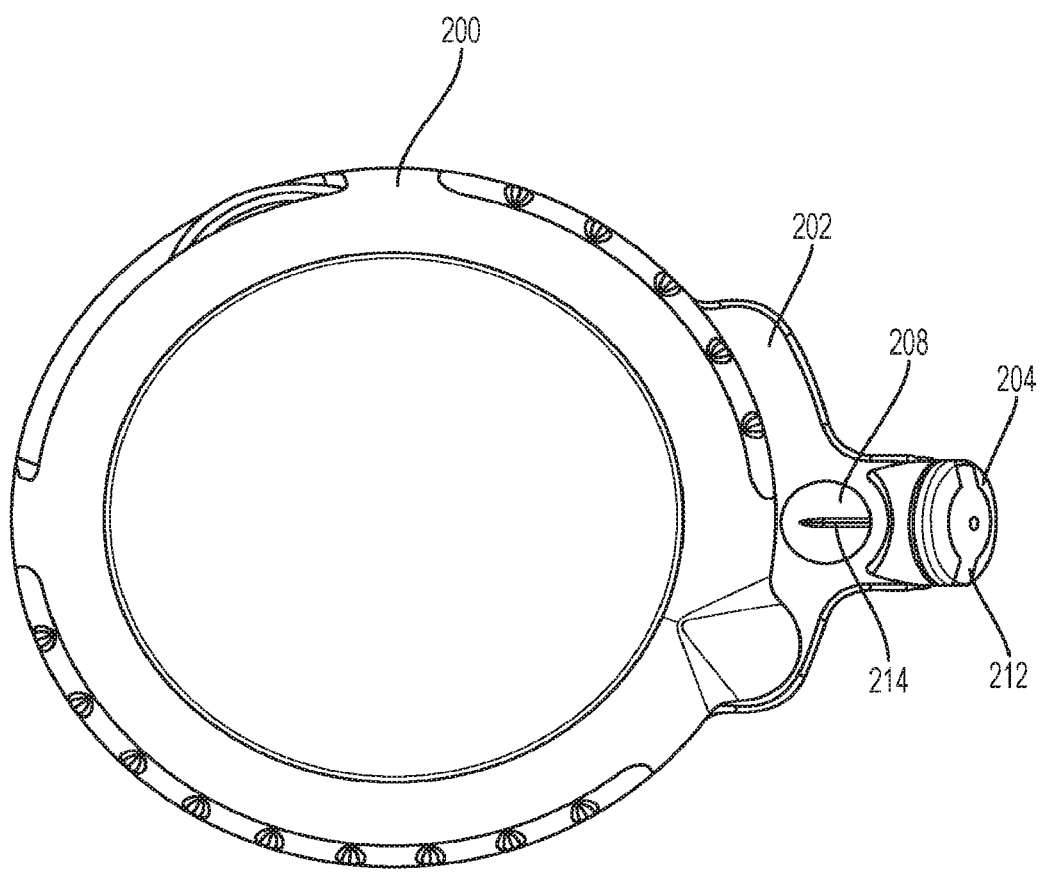
Figure 4J:
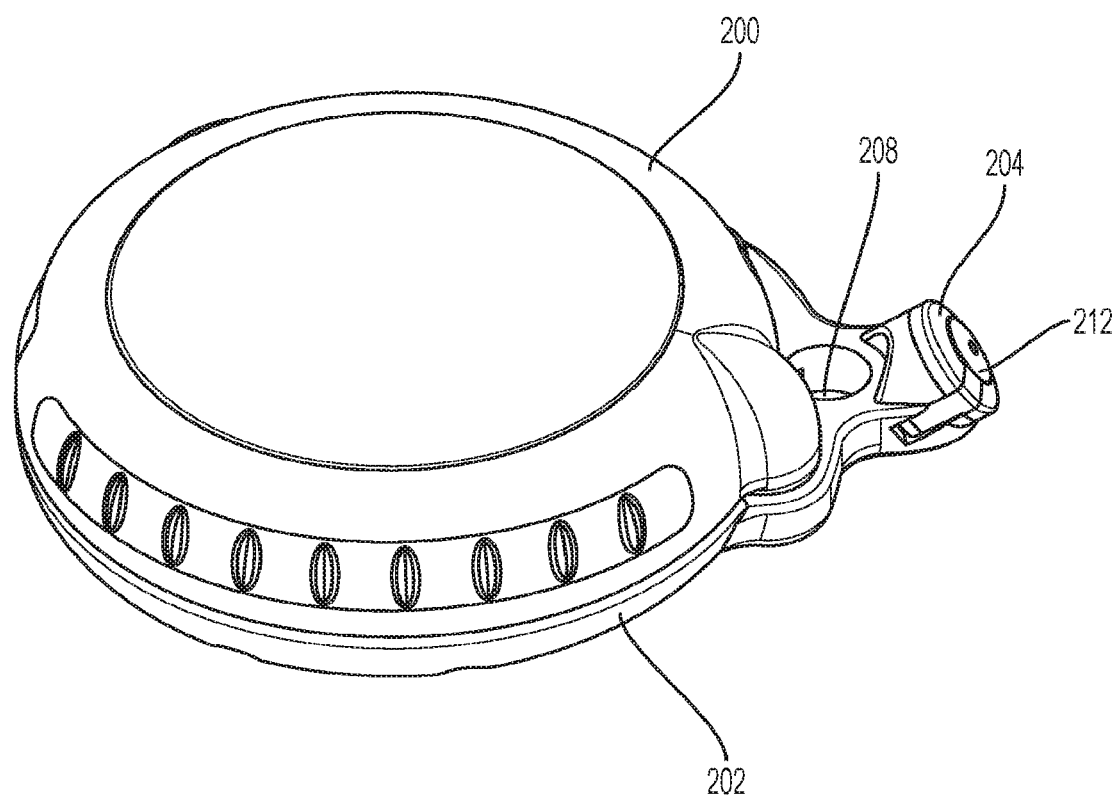
Figure 4K:
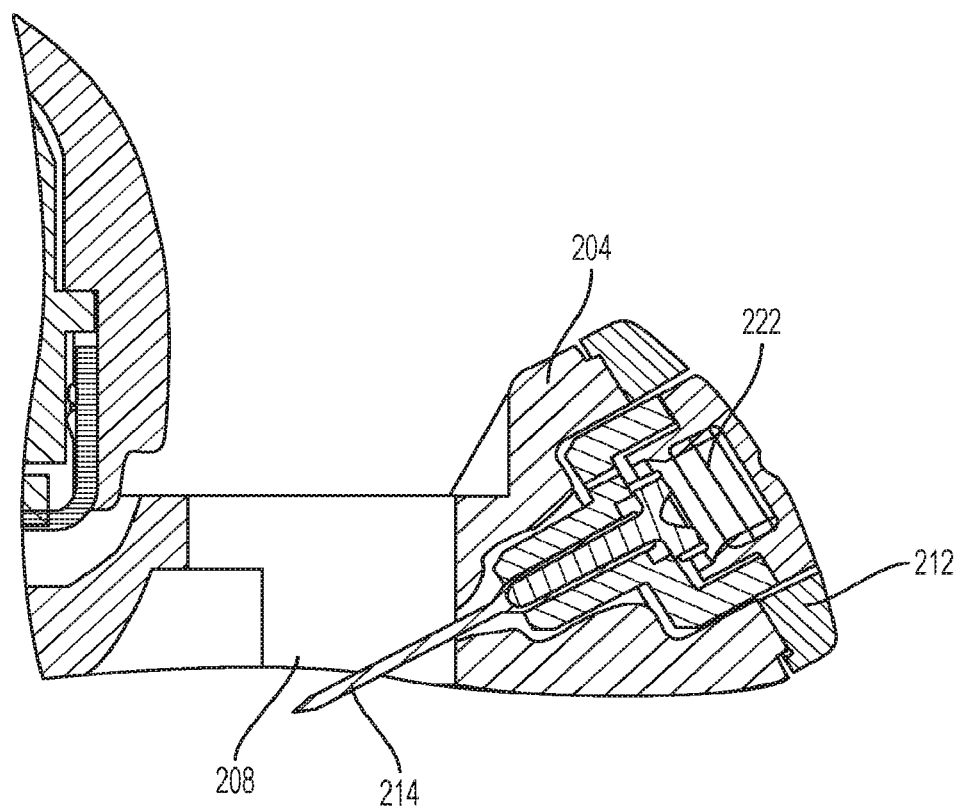
Figure 5A:
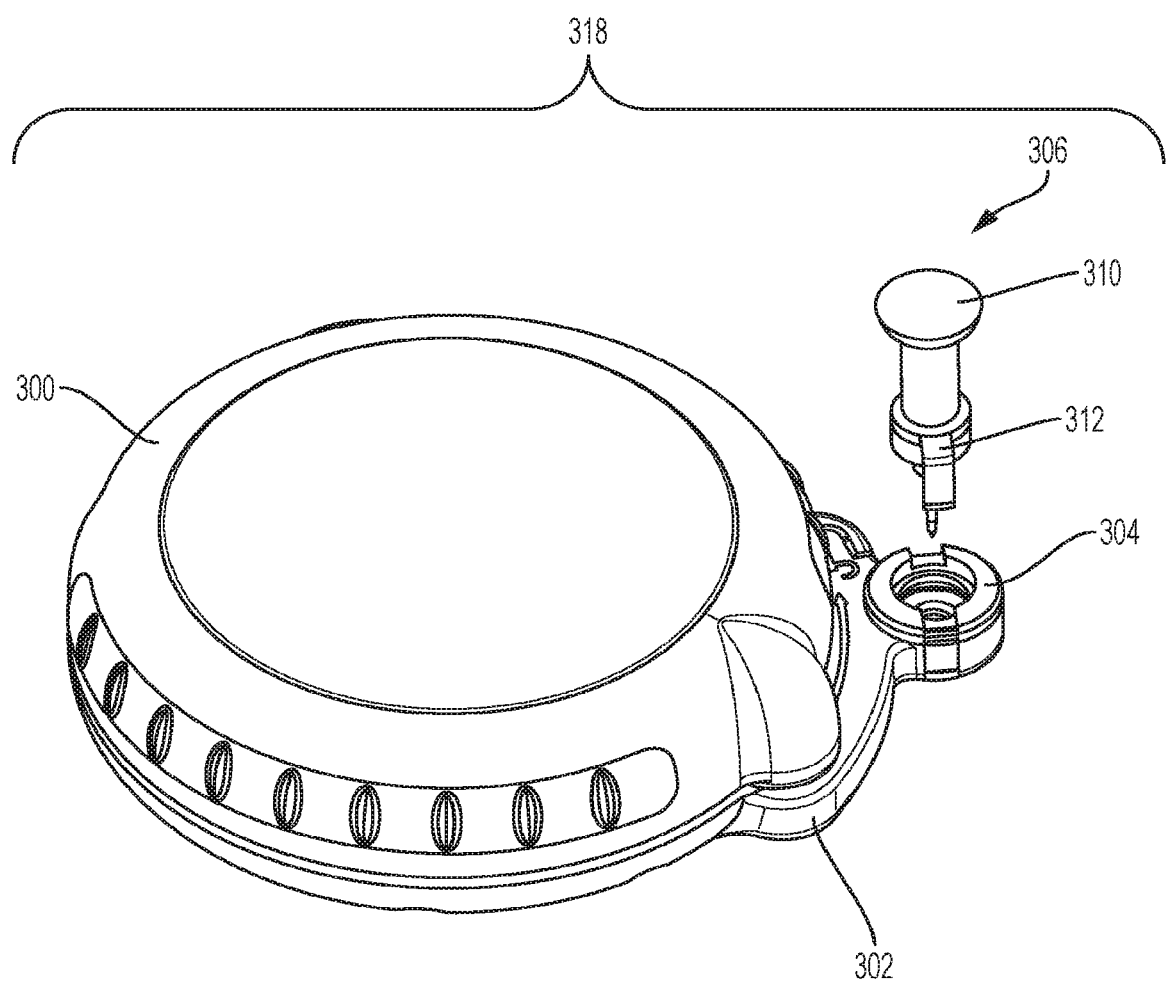
FIGS. 5A-5F are various views of one embodiment of an infusion device system.
Figure 5B:
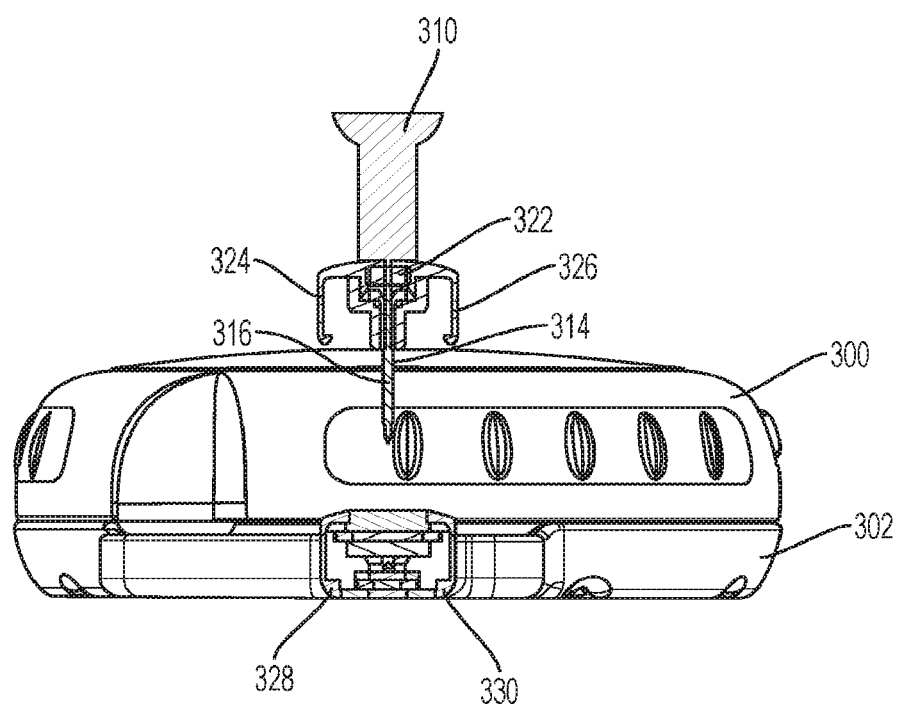
Figure 5C:
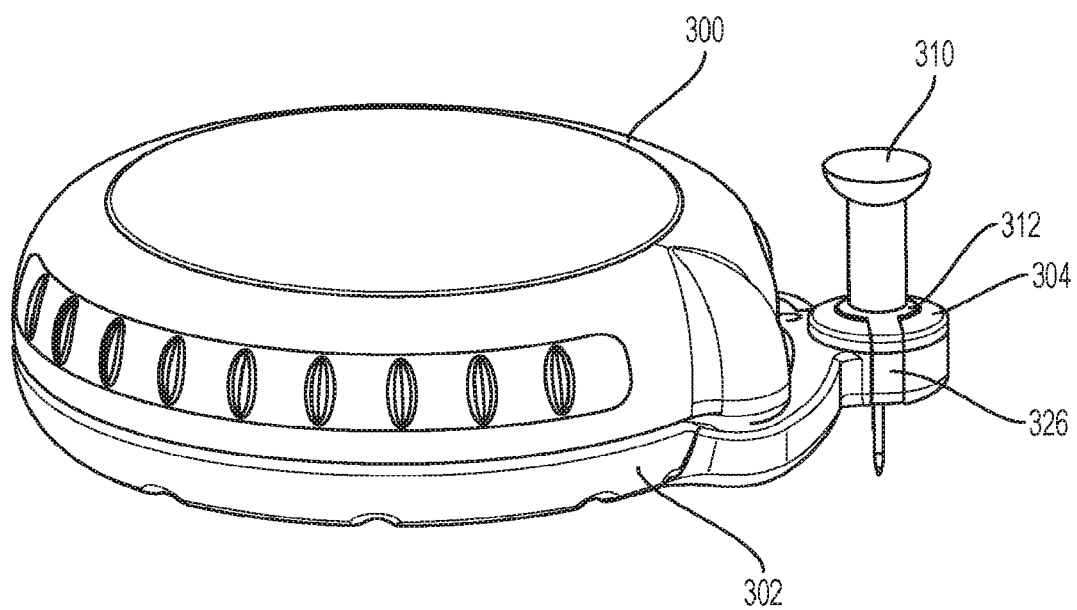
Figure 5D:
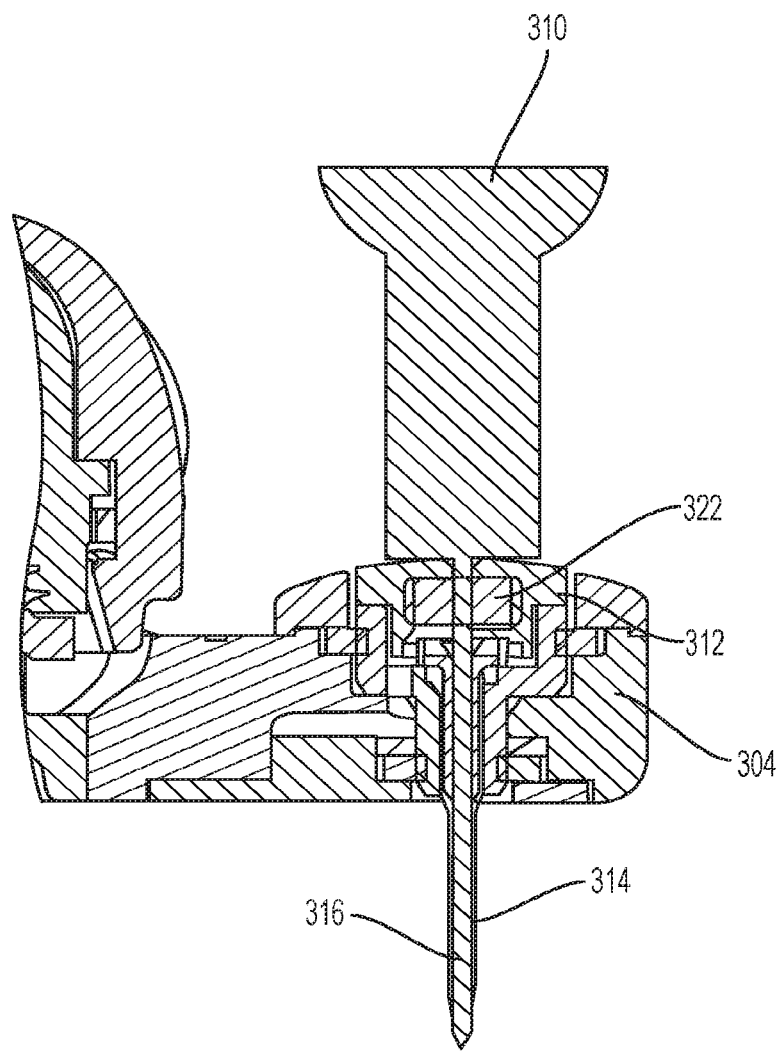
Figure 5E:
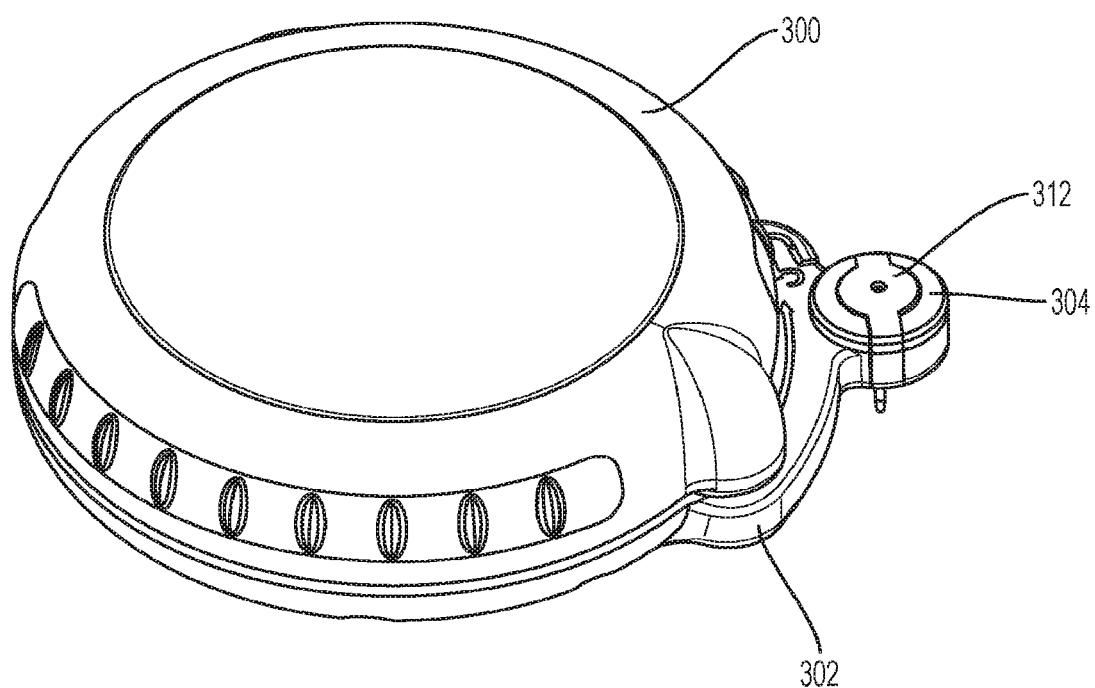
Figure 5F:
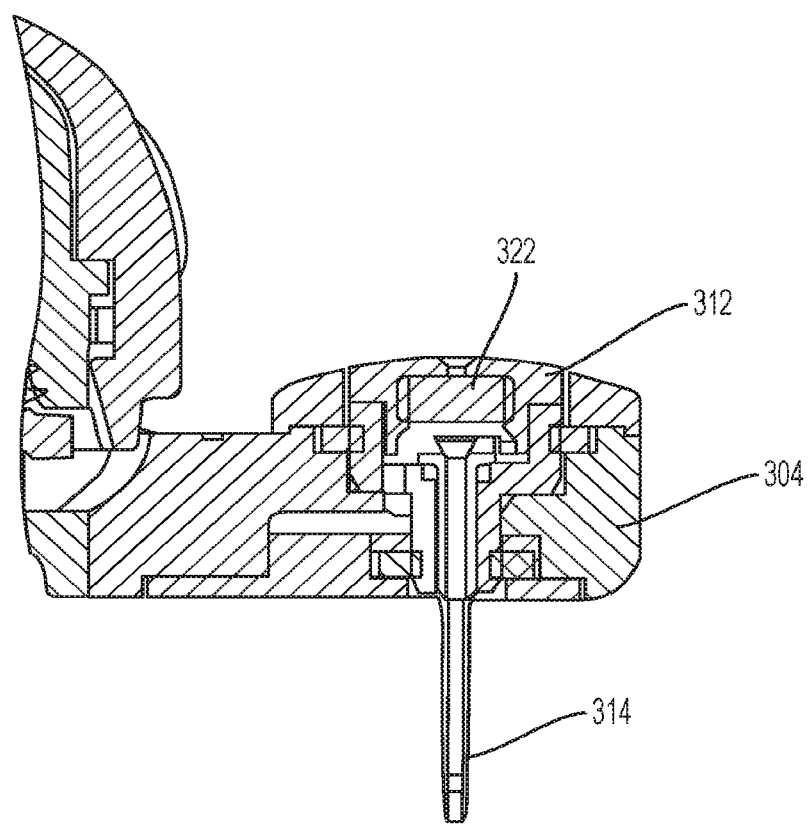
Figure 6A:
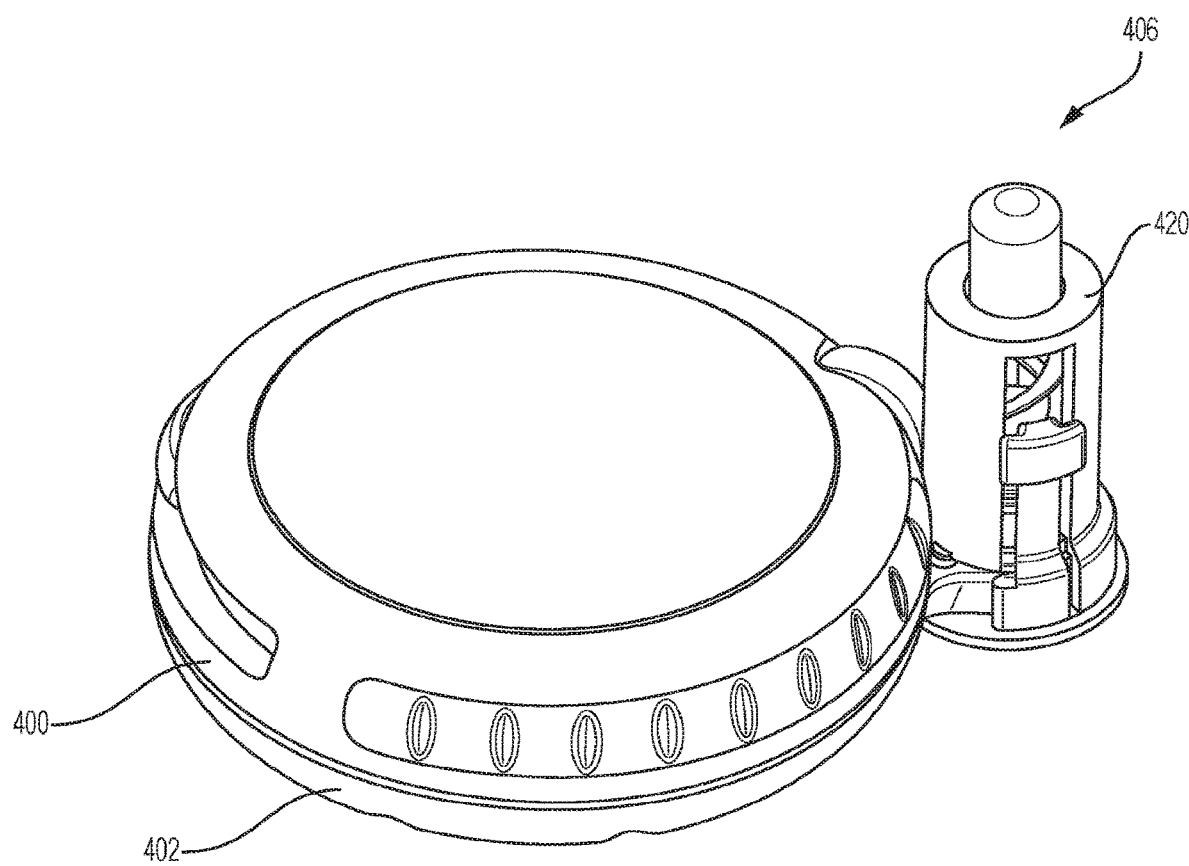
FIGS. 6A-6G are various views of one embodiment of an infusion device system.
Figure 6B:
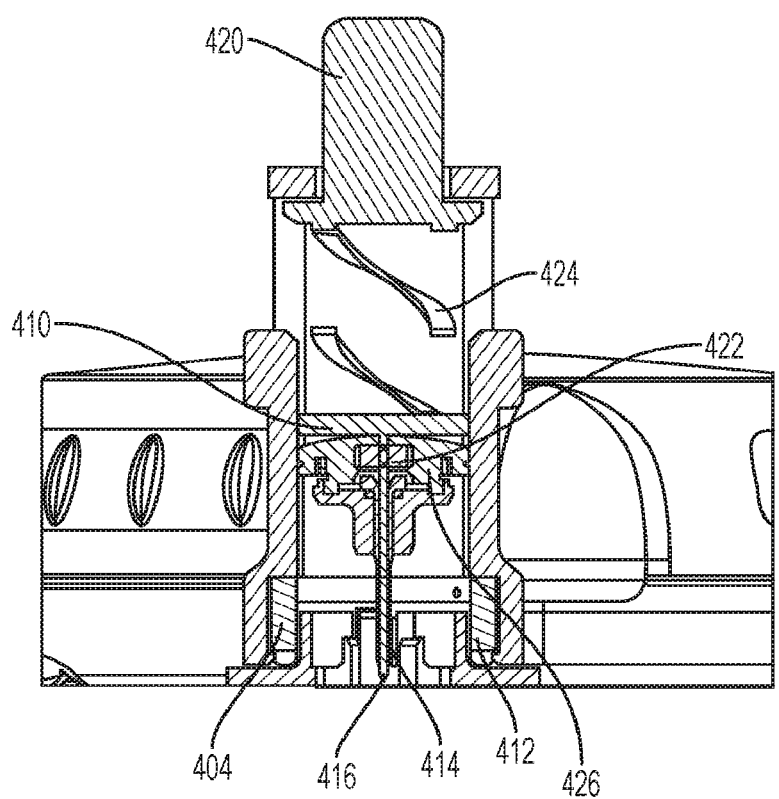
Figure 6C:
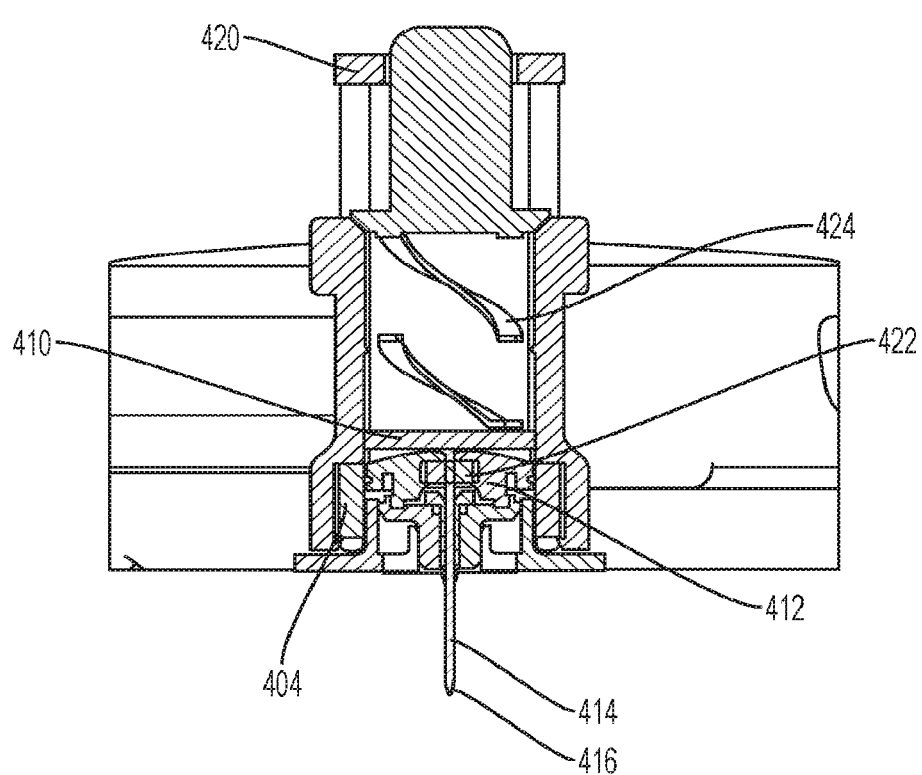
Figure 6D:
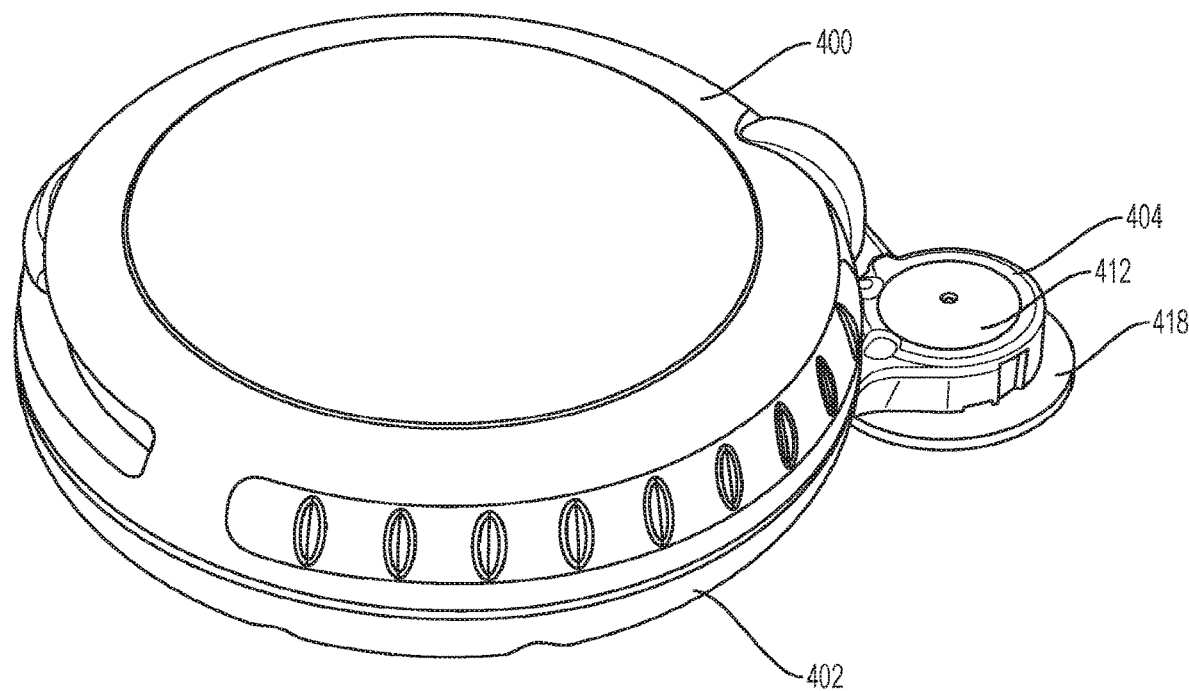
Figure 6E:
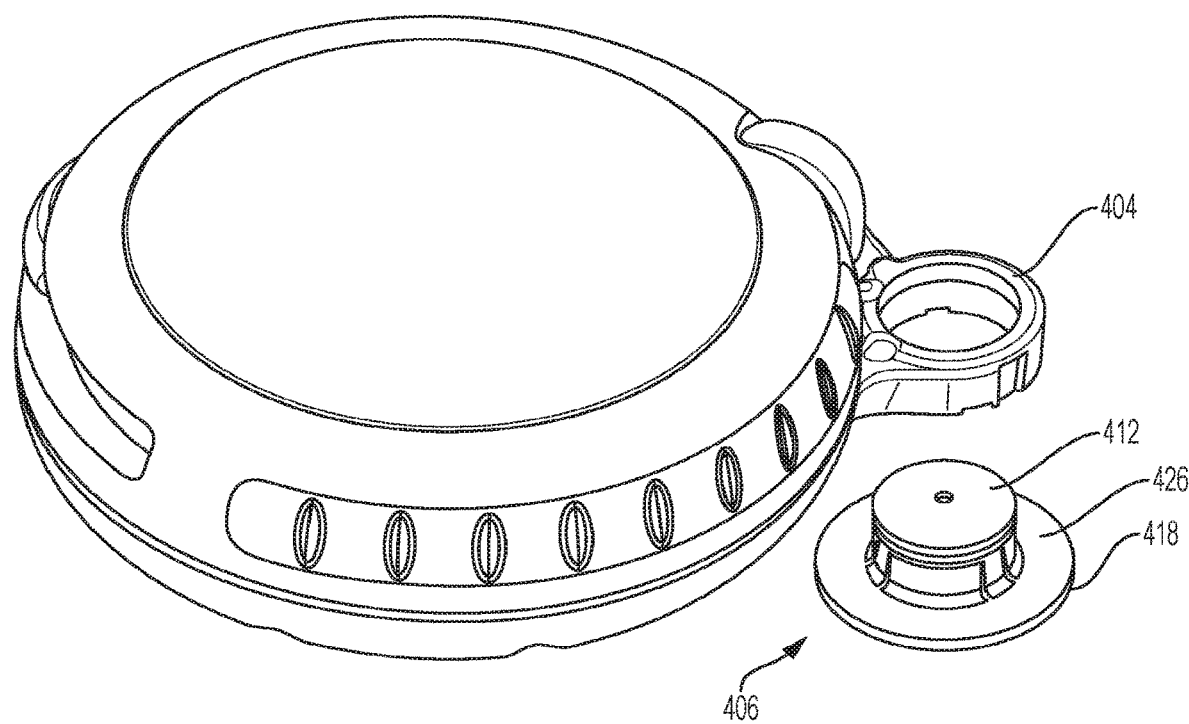
Figure 6F:
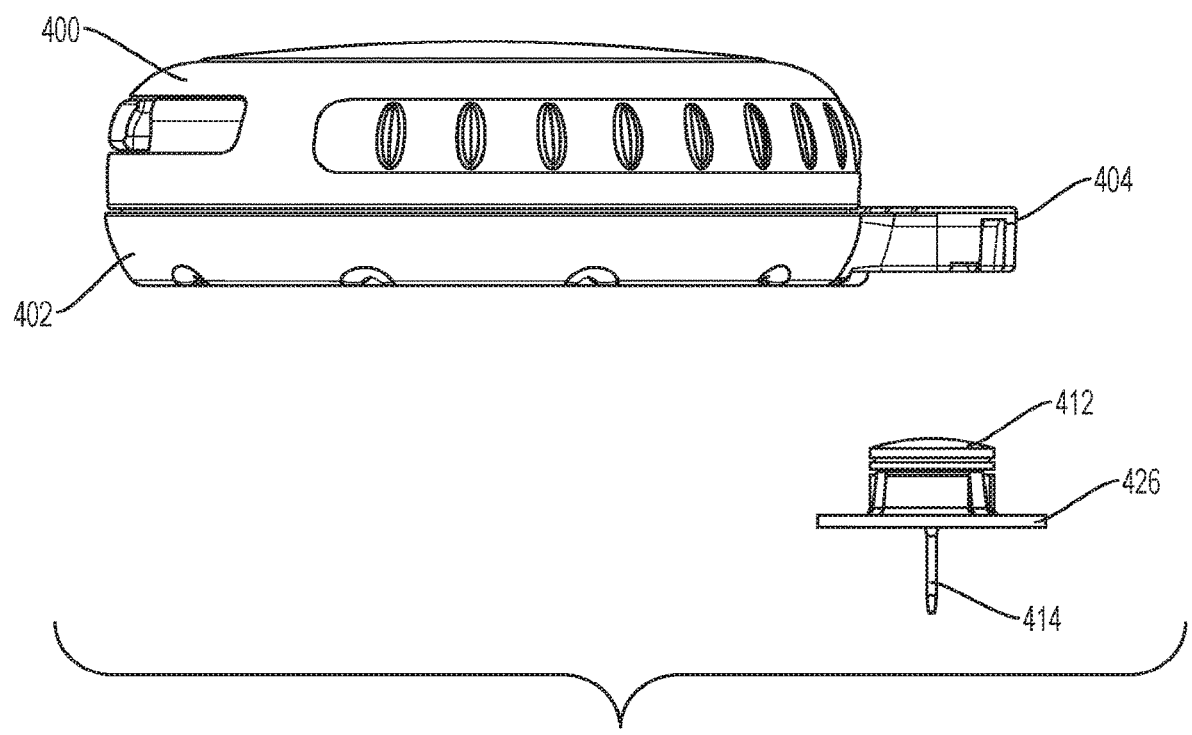
Figure 6G:
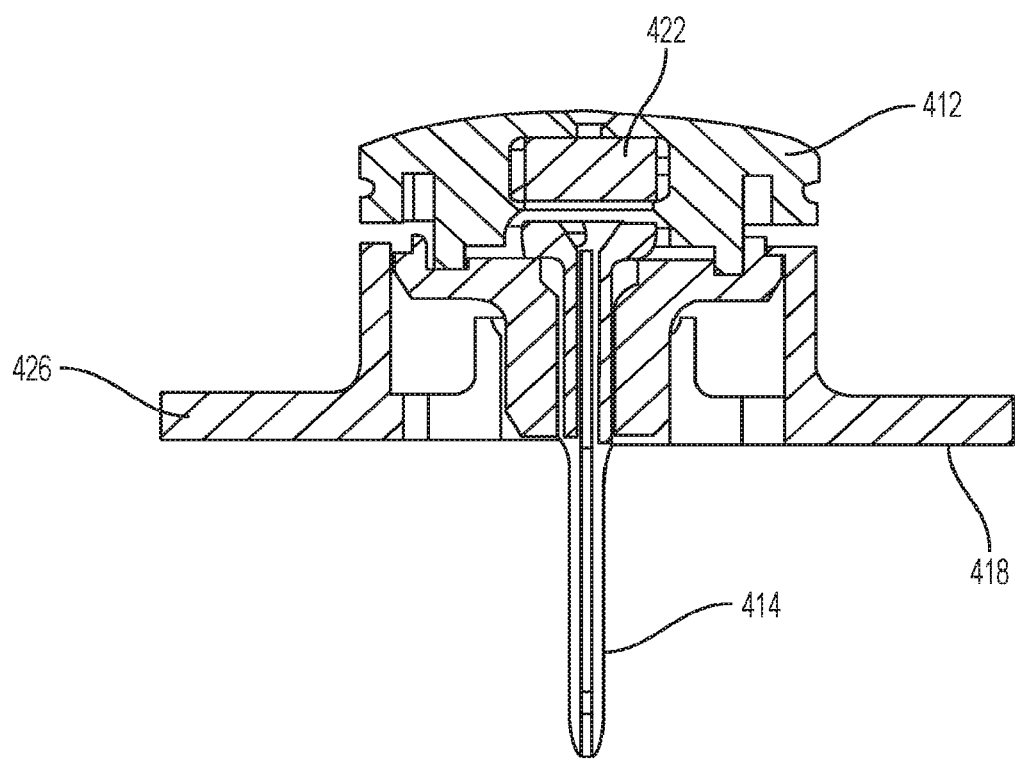

In various embodiments, an infusion device and system and methods thereof is disclosed. The infusion device is configured to be inserted into the subcutaneous layer of a user's skin and be fluidly connected to a fluid source. In various embodiments, the infusion device may be fluidly connected to a length of tubing and/or to an infusion pump. Infusion pumps include any infusion pump which may include, but is not limited to, the various infusion pumps shown and described in U.S. patent application Ser. No. 13/788,260, filed Mar. 7, 2013 and entitled Infusion Pump Assembly, now U.S. Publication No. US-2014-0107579, published Apr. 17, 2014; U.S. Pat. No. 8,491,570, issued Jul. 23, 2013 and entitled Infusion Pump Assembly; U.S. Pat. No. 8,414,522, issued Apr. 9, 2013 and entitled Fluid Delivery Systems and Methods; U.S. Pat. No. 8,262,616, issued Sep. 11, 2012 and entitled Infusion Pump Assembly; and U.S. Pat. No. 7,306,578, issued Dec. 11, 2007 and entitled Loading Mechanism for Infusion Pump; all of which are hereby incorporated herein by reference in their entireties. In various embodiments, the various embodiments of the infusion devices described herein may be used alone or in conjunction with an autoinserter.

In various embodiments, an infusion device is disclosed that includes an introduction needle and a cannula but, in various embodiments, includes embodiments that do not include additional tubing connected to a fluid source. Rather, in these embodiments, the cannula is directly fluidly connected to a fluid source. This may be desirable/beneficial for many reasons, including but not limited to, the ability to infuse fluids subcutaneously without the hassles and inconvenience of additional tubing which has various downsides including, but not limited to, being caught, getting tangled, becoming occluded, and difficulty in concealing the tubing for everyday use. However, in some embodiments, the system described herein includes the option of fluidly attaching tubing to the cannula. Additionally, some embodiments include an autoinserter while other embodiments do not. Embodiments without an autoinserter may be beneficial/desirable for many reasons, including, but not limited to, the size of the infusion device may be minimized and the simplicity of the infusion device may minimize costs to both manufacturers and users.

Referring now to FIGS. 1A-3C, in various embodiments, the infusion device system 108 may include an infusion device 106 which in various embodiments may include a top portion 110, a bottom portion 112, a cannula 114, an introduction needle 116 and an adhesive strip 118. The introduction needle 116 is attached to the top portion 110 and the cannula 114 is attached to the bottom portion 112. In various embodiments, the top portion 110 may be configured such that it is easily maneuvered by a user and/or caregiver. Although the size and shape of the top portion 110 may vary in various embodiments, in some embodiments, the size and shape are ergonomic and easily maneuverable to complete the insertion of the cannula 114 by a user and/or caregiver. In various embodiments, inside the bottom portion 112 is a septum 122 in which the instroduction needle pierces through in the starting position, which is shown in, for example, FIGS. 1A-1C. In various embodiments, the infusion device system 108 may also include a fluid source which in some embodiments may be an infusion pump assembly/apparatus which may include a disposable housing assembly 102 and a reusable housing assembly 100. In various embodiments, the disposable housing assembly 102 and resusable housing assembly 100 are configured to be removably attached to one another.

Referring now also to FIGS. 7A-7B & 8-9, there are shown various views of infusion pump assembly 500, which is shown to include reusable housing assembly 502, switch assembly 506, and main body portion 508. In various embodiments, main body portion 508 may include a plurality of components, examples of which may include but are not limited to a volume sensor assembly 548, printed circuit board 600, vibration motor assembly 602, shape memory actuator anchor 604, switch assembly 506, battery 606, antenna assembly 608, pump assembly 106, measurement valve assembly 610, volume sensor valve assembly 612 and reservoir valve assembly 614. To enhance clarity, printed circuit board 600 has been removed from FIG. 7B to allow for viewing of the various components positioned beneath printed circuit board 600.

The various electrical components that may be electrically coupled with printed circuit board 600 may utilize spring-biased terminals that allow for electrical coupling without the need for soldering the connections. For example, vibration motor assembly 602 may utilize a pair of spring-biased terminals (one positive terminal and one negative terminal) that are configured to press against corresponding conductive pads on printed circuit board 600 when vibration motor assembly 602 is positioned on printed circuit board 600. However, in the exemplary embodiment, vibration motor assembly 602 is soldered directly to the printed circuit board.

The volume sensor assembly 548 may be configured to monitor the amount of fluid infused by infusion pump assembly 500. For example, volume sensor assembly 548 may employ acoustic volume sensing, which is the subject of U.S. Pat. Nos. 5,575,310 and 5,755,683 assigned to DEKA Products Limited Partnership, as well as the U.S. Pat. No. 8,414,522, issued Apr. 9, 2013, and entitled Fluid Delivery Systems and Methods; U.S. Pat. No. 8,545,445, issued Oct. 1, 2013, and entitled Patch-Sized Fluid Delivery Systems and Methods and U.S. Pat. No. 8,113,244, issued Feb. 14, 2012, and entitled Adhesive and Peripheral Systems and Methods for Medical Devices, the entire disclosures of all of which are incorporated herein by reference.

Vibration motor assembly 602 may be configured to provide a vibration-based signal to the user of infusion pump assembly 500. For example, in the event that the voltage of battery 606 (which powers infusion pump assembly 500) is below the minimum acceptable voltage, vibration motor assembly 602 may vibrate infusion pump assembly 500 to provide a vibration-based signal to the user of infusion pump assembly 500. Shape memory actuator anchor 604 may provide a mounting point for the above-described shape memory actuator (e.g. shape memory actuator 512). In various embodiments, shape memory actuator 512 may be, for example, a conductive shape-memory alloy wire that changes shape with temperature. The temperature of shape-memory actuator 512 may be changed with a heater, or more conveniently, by application of electrical energy. Accordingly, one end of shape memory actuator 512 may be rigidly affixed (i.e., anchored) to shape memory actuator anchor 604 and the other end of shape memory actuator 512 may be applied to e.g. a valve assembly and/or a pump actuator. Therefore, by applying electrical energy to shape memory actuator 512, the length of shape memory actuator 512 may be controlled and, therefore, the valve assembly and/or the pump actuator to which it is attached may be manipulated. Various methods and systems related to the control and actuation of shape memory actuator 512 and shape memory alloys are described in U.S. patent application Ser. No. 12/837,193, filed Jul. 15, 2010 and entitled Apparatus, Systems and Methods for an Infusion Pump Assembly, now U.S. Publication No. US-2011-0144574, published Jun. 16, 2011; U.S. Pat. No. 8,852,164, issued Oct. 7, 2014, and entitled Method and System for Shape-Memory Alloy Wire Control and U.S. Pat. No. 8,579,884, issued Nov. 12, 2013 and entitled Infusion Pump Assembly each of which is incorporated herein by reference in its entirety.

Antenna assembly 608 may be configured to allow for wireless communication between e.g. infusion pump assembly 500 and a remote control assembly (not shown). The remote control assembly may allow the user to program infusion pump assembly 500 and e.g. configure bolus and basal infusion events. As discussed above, infusion pump assembly 500 may include one or more valve assemblies configured to control the flow of the infusible fluid through a fluid path 524 (within infusion pump assembly 500) and pump assembly 526A, located in the reusable housing assembly 502, may be configured to pump the infusible fluid from the fluid path 524 to the user, and in various embodiments, pumps fluid from the reservoir, into the pumping chamber 526B (located in the disposable housing assembly 504). In this particular embodiment of infusion pump assembly 500, infusion pump assembly 500 is shown to include three valve assemblies, namely measurement valve assembly 610, volume sensor valve assembly 612, and reservoir valve assembly 614.

As discussed above and referring also to FIG. 9, the infusible fluid may be stored within reservoir 518. In order to effectuate the delivery of the infusible fluid to the user, the processing logic (not shown) included within infusion pump assembly 500 may energize shape memory actuator 512, which may be anchored on one end using shape memory actuator anchor 604. Shape memory actuator 512 may result in the activation of pump assembly 526A and reservoir valve assembly 614. Reservoir valve assembly 614 may include reservoir valve actuator 614A and reservoir valve 614B, and the activation of reservoir valve assembly 614 may result in the downward displacement of reservoir valve actuator 614A and the closing of reservoir valve 614B, resulting in the effective isolation of reservoir 518. Further, pump assembly 526A may include a pump plunger and pump chamber 526B and the activation of the pump assembly 526A may result in pump plunger being displaced in a downward fashion into pump chamber 526B and the displacement of the infusible fluid (in the direction of arrow 616).

Volume sensor valve assembly 612 may include volume sensor valve actuator 612A and volume sensor valve 612B. In various embodiments, volume sensor valve actuator 612A may be closed via a spring assembly that provides mechanical force to seal volume sensor valve 612B. However, when pump assembly 526A is activated, if the displaced infusible fluid is of sufficient pressure to overcome the mechanical sealing force of volume sensor valve assembly 612, the displacement of the infusible fluid occurs in the direction of arrow 618. This may result in the filling of volume sensor chamber 620 included within volume sensor assembly 548. Through the use of speaker assembly 622, port assembly 624, reference microphone 626, spring diaphragm 628, invariable volume microphone 630, volume sensor assembly 548 may determine the volume of infusible fluid included within volume sensor chamber 620.

Figure 8:
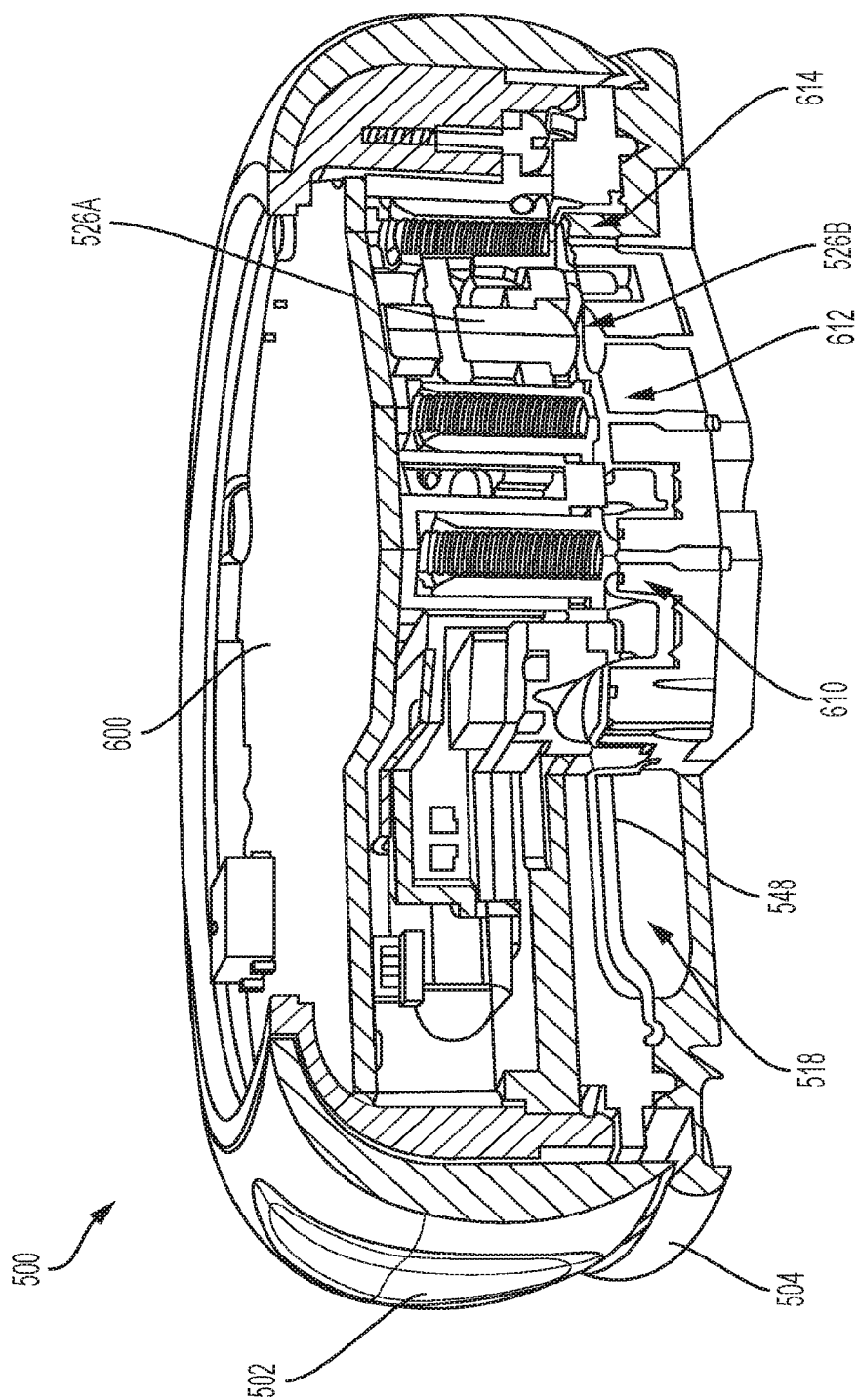
FIG. 8 is a cross-sectional view of an embodiment of a disposable housing assembly of an embodiment of an infusion pump assembly.
Figure 9:
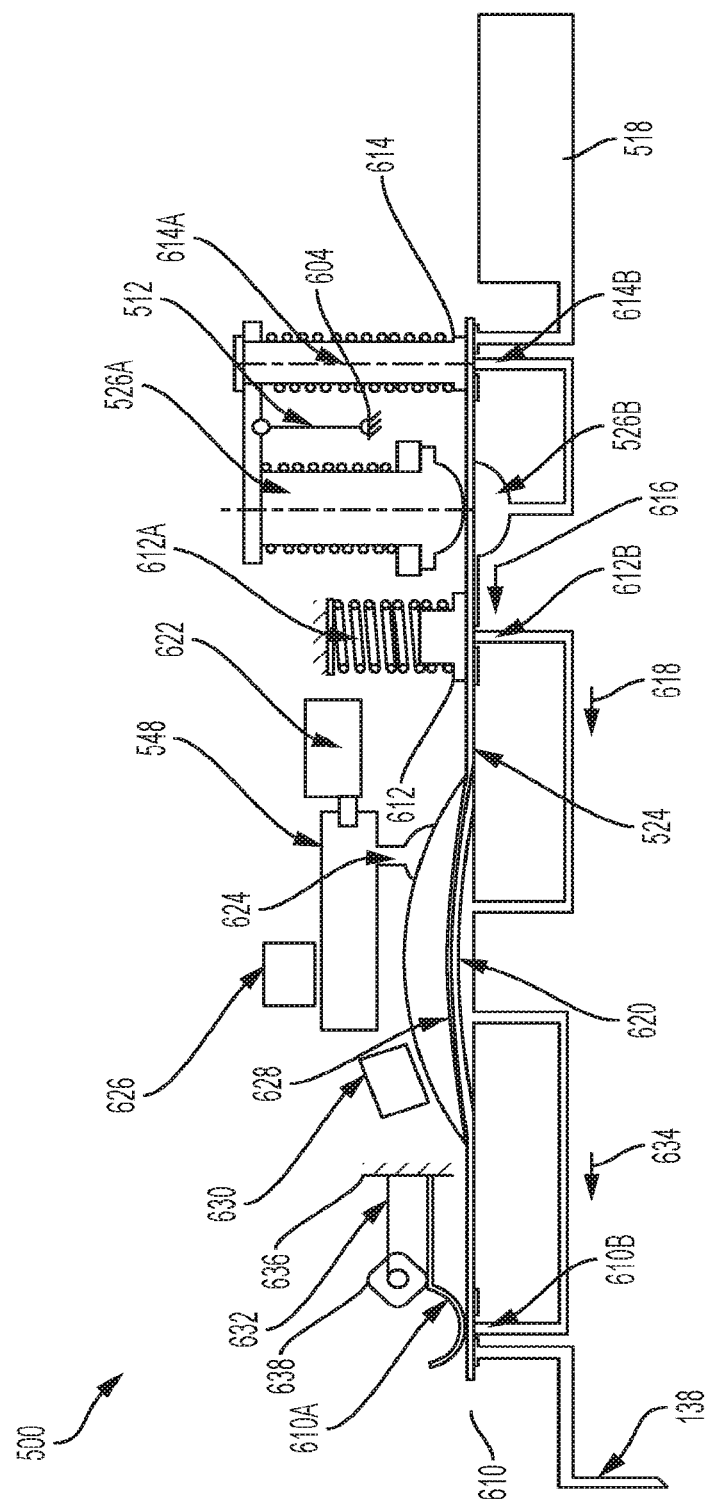
FIG. 9 is a diagrammatic view of a fluid path within an embodiment of the infusion pump assembly.

In various embodiments, the disposable housing assembly may be any of the embodiment described herein or incorporated by reference. In any one or more of the embodiments of the disposable housing assembly, the disposable housing assembly includes a reservoir. An embodiment of the reservoir is shown in FIG. 8, however, this embodiment of the reservoir is not limited to the embodiment of the disposable housing assembly shown in FIG. 8. Rather, the reservoir is included, even if not shown, in all embodiments of the disposable housing assembly. Further, the various embodiments of the disposable housing assembly described herein may be used with any of the various embodiments of the infusion device described herein and therefore, each embodiment of the infusion device system is not limited only to the embodiment of the disposable housing assembly shown and described with respect to that particular embodiment of the infusion device.

Referring also to FIGS. 1A-3C, in various embodiments, and as discussed above, the disposable housing assembly 102 includes a reservoir 518 and an infusion device mating assembly 104. The infusion device mating assembly 104 includes a piercing needle 120 which passes through the opening 124 on the bottom portion 112 of the infusion device 106. The piercing needle 120 is fluidly connected to the reservoir 518.

In practice, the infusion device 106 is pushed into the subcutaneous skin layer of a user by applying a downward force to the top portion 110 of the infusion device 106. The introduction needle 116 pierces the skin and provides entry for the cannula 114. Once this is completed, the top portion 110 may be removed from the bottom portion 112 by applying an opposite force onto the top portion 110. The top portion 110 and introduction needle 116 are then removed from the bottom portion 112 and the user. The adhesive strip 118 maintains the location of the bottom portion 112 on the skin of the user.

In various embodiments, the adhesive strip 118 may be any size and shape, including, but not limited to, the size and shape shown in FIGS. 1A-3C.

The disposable housing assembly 102 infusion device mating assembly 104 may be mated with the bottom portion 112 of the infusion device 106 by placing the infusion device mating assembly 104 on top of the bottom portion 112 and the application of force in the direction towards the bottom portion 112. In various embodiments, the application of force causes a piercing needle 120 to pierce a septum which, in some embodiments, is located in the opening 124. The application of force eases the piercing needle 120 through the opening 124 and the piercing needle 120 fluidly connects to the cannula 114, which, in various embodiments, fluidly connects the reservoir 518 to the cannula 114. In various embodiments, the infusion device mating assembly 104 may be attached to the bottom portion 112 in any orientation, thus, the user may place the disposable housing assembly 102 in any orientation i.e., within 360 degrees, with respect to the bottom portion 112.

In various embodiments of this embodiment of the infusion device system 108, if and when a user wishes to move the location of the disposable housing assembly 102, the infusion device mating assembly 104 may be removed from the bottom portion 112 and the bottom portion 112 and cannula 114 may be removed from the user. Following, the user may connect another infusion device 106 bottom portion 112 to their skin in a different location on their body and reconnect the disposable housing assembly 102 infusion device mating assembly 104. In some embodiments, rather than removing the bottom portion 112 and the cannula 114, the infusion device system may include a tubing or other that connects to the bottom portion 112 on a first end of the tubing and to the infusion device mating assembly 104 on the second end of the tubing, thereby creating a fluid connection between the disposable housing assembly 102 and the cannula 114 without the need for removing a first cannula and inserting a second cannula.

Referring now also to FIGS. 4A-4K, in various embodiments, the infusion device system 218 may include an infusion device 206 which in various embodiments may include a top portion 210, a bottom portion 212, a cannula 214 and an introduction needle 216. The introduction needle 216 is attached to the top portion 210 and the cannula 214 is attached to the bottom portion 212. Inside the bottom portion 212 is a septum 222 in which the introduction needle 216 pierces through in the starting position, which is shown in, for example, FIGS. 4A-4E. In various embodiments, the infusion device system 218 may also include a fluid source which in some embodiments may be an infusion pump apparatus which includes a disposable housing assembly 202 and a reusable housing assembly 200. In various embodiments, the disposable housing assembly 202 includes a reservoir 518 and an infusion device mating assembly 204.

In practice, the infusion device 206 is pushed into the subcutaneous skin layer of a user by applying a downward force to the top portion 210 of the infusion device 206. The introduction needle 216 pierces the skin and provides entry for the cannula 214. Once this is completed, the top portion 210 may be removed from the bottom portion 212 by applying an opposite force onto the top portion 210. The top portion 210 and introduction needle 216 are then removed from the bottom portion 212 and the user.

In various embodiments, the infusion device 206 may be inserted into a user through a disposable housing assembly 202 infusion device mating assembly 204. In these embodiments, the infusion device 206 is connected to the infusion device mating assembly 204 and the bottom portion 212 of the infusion device 206 is attached to the infusion device mating assembly 204. The attachment mechanism may be any mechanism, and in some embodiments, may include one or more locking fingers 224, 226 which, in various embodiments, may be spring loaded and when the bottom portion 212 is placed onto the infusion device mating assembly 204, the locking fingers 224, 226 lock into receiving areas 228, 230 on the infusion device mating assembly 204 configured to receive and retain the locking fingers 224, 226. In various embodiments, the receiving areas 228, 230 may be grooves, however, in various other embodiments, the receiving areas 228, 230 may vary and in various embodiments including other embodiments of attachment mechanisms, the receiving features may vary. The top portion 210 may then be separated from the bottom portion 212 by application of force in the direction away from the infusion device mating assembly 204. When the top portion 210 is separated from the bottom portion 212, the introduction needle 216 is removed from the cannula 214, leaving the cannula 214 inserted inside the user (or not inserted into a user).

In various embodiments, attaching the bottom portion 212 to the infusion device mating assembly 204 forms a fluid connection between the reservoir 518 in a disposable housing assembly 202 and the cannula 214.

In various embodiments of the infusion device system 218, the disposable housing assembly 202 may include a viewing opening 208 located adjacent to the infusion device mating assembly 204 allowing the user or a caregiver to view the cannula 214. This may be desirable/beneficial for many reasons, including, but not limited to, the ability to view the status of the cannula 214 that is inserted in the user. This may be desirable/beneficial for many reasons, including, but not limited to, the ability to determine whether the cannula 214 has become dislodged or if there is blood or other indication of a potential occlusion within the cannula.

Although the embodiments shown in FIGS. 4A-4K show an infusion device 206 inserted at an angle, and the infusion device mating assembly 204 is also at an angle with respect to the disposable housing assembly 202 and reusable housing assembly 200, in various embodiments, the infusion device mating assembly 204, disposable housing assembly 202 and reusable housing assembly 200 may be configured such that the infusion device 206 is inserted perpendicular to the infusion device mating assembly 204, disposable housing assembly 202 and reusable housing assembly 200.

Referring now also to FIGS. 5A-5F in various embodiments, the infusion device system 318 may include an infusion device 306 which in various embodiments may include a top portion 310, a bottom portion 312, a cannula 314 and an introduction needle 316. The introduction needle 316 is attached to the top portion 310 and the cannula 314 is attached to the bottom portion 312. Inside the bottom portion 312 is a septum 322 in which the introduction needle 316 pierces through in the starting position, which is shown in, for example, FIGS. 5A-5B. In various embodiments, the infusion device system 318 may also include a fluid source which in some embodiments may be an infusion pump apparatus which includes a disposable housing assembly 302 and a reusable housing assembly 300. In various embodiments, the disposable housing assembly 302 includes a reservoir 518 and an infusion device mating assembly 304.

In practice, the infusion device 306 is pushed into the subcutaneous skin layer of a user by applying a downward force to the top portion 310 of the infusion device 306. The introduction needle 316 pierces the skin and provides entry for the cannula 314. Once this is completed, the top portion 310 may be removed from the bottom portion 312 by applying an opposite force onto the top portion 310. The top portion 310 and introduction needle 316 are then removed from the bottom portion 312 and the user.

In various embodiments, the infusion device 306 may be inserted into a user through a disposable housing assembly 302 infusion device mating assembly 304. In these embodiments, the infusion device 306 is connected to the infusion device mating assembly 304 and the bottom portion 312 of the infusion device 306 is attached to the infusion device mating assembly 304. The attachment mechanism may be any mechanism, and in some embodiments, may include one or more locking fingers 324, 326 which, in various embodiments, may be spring loaded and when the bottom portion 312 is placed onto the infusion device mating assembly 304, the locking fingers 324, 326 lock into receiving areas 328, 330 on the infusion device mating assembly 304 configured to receive and retain the locking fingers 324, 326. In various embodiments, the receiving areas 328, 330 may be grooves, however, in various other embodiments, the receiving areas 328, 330 may vary and in various embodiments including other embodiments of attachment mechanisms, the receiving features may vary. The top portion 310 may then be separated from the bottom portion 312 by application of force in the direction away from the infusion device mating assembly 304. When the top portion 310 is separated from the bottom portion 312, the introduction needle 316 is removed from the cannula 314, leaving the cannula 314 inserted inside the user (or not inserted into a user).

In various embodiments, attaching the bottom portion 312 to the infusion device mating assembly 304 forms a fluid connection between a reservoir 518 in a disposable housing assembly 302 and the cannula 314.

In various embodiments of the infusion device system 318, the disposable housing assembly 302 may include a viewing opening (see for example, FIG. 4, item 208) allowing the user or a caregiver to view the cannula 314. This may be desirable/beneficial for many reasons, including, but not limited to, the ability to view the status of the cannula 314 that is inserted in the user. This may be desirable/beneficial for many reasons, including, but not limited to, the ability to determine whether the cannula 314 has become dislodged or if there is blood or other indication of a potential occlusion within the cannula.

Although the embodiments shown in FIGS. 5A-5F show an infusion device 206 inserted perpendicular with respect to the disposable housing assembly 302, the reusable housing assembly 300, and the infusion device mating assembly 304, in various embodiments, the infusion device mating assembly 304, disposable housing assembly 302 and reusable housing assembly 300 may be configured such that the infusion device 306 is inserted at an angle to the infusion device mating assembly 304, disposable housing assembly 302 and reusable housing assembly 300.

Referring now also to FIGS. 6A-6G in various embodiments the infusion device system may include an infusion device 406 which in various embodiments may include a top portion 412, a bottom portion 426, a cannula 414, an introduction needle 416 and an adhesive strip 418. The introduction needle 416 is attached to the top portion 412 and the cannula 414 is attached to the bottom portion 426. In various embodiments, the top portion 412 may be configured such that it may be attached to an autoinserter 420. Although the size and shape of the top portion 412 may vary in various embodiments, in some embodiments, the size and shape is configured such that it may be used within an autoinserter 420. In various embodiments, inside the bottom portion 426 is a septum 422 in which the introduction needle 416 pierces through. In various embodiments, the infusion device system may also include a fluid source which in some embodiments may be an infusion pump apparatus which includes a disposable housing assembly 402 and a reusable housing assembly 400. In various embodiments, the disposable housing assembly 402 includes a reservoir 518 and an infusion device mating assembly 404.

In practice, the infusion device 406 is pushed into the subcutaneous skin layer of a user by applying a downward force to the top portion 412 of the infusion device 406. The introduction needle 416 pierces the skin and provides entry for the cannula 414. Once this is completed, the introduction needle 416 may be removed from the bottom portion 412 by applying an opposite force onto the introduction needle 416. The introduction needle 416 is then removed from the bottom portion 412 and the user. The adhesive strip 418 maintains the location of the bottom portion 418 on the skin of the user.

In various embodiments, the downward force is generated by the autoinserter 420 which, in various embodiments, includes a spring 424 and a mechanism that releases the spring 424 which forces a push plate 410 downward. This action drives the push plate 410 into the bottom portion 412. Once the push plate 410 is connected with the bottom portion 412, the autoinserter 420 may be removed, leaving the bottom portion 412 of the inserter device 406 attached to the user by way of the adhesive strip 418. In various embodiments, a mechanism may be used that pulls the push plate 410 back into the autoinserter 420 and therefore, in these embodiments, the autoinserter 420 serves as a container for the introduction needle 416. In various embodiments, the adhesive strip 418 may be any size and shape, including, but not limited to, the size and shape shown in FIGS. 6A-6G.

The disposable housing assembly 402 infusion device mating assembly 404 may be mated with the bottom portion 412 of the infusion device 406 by placing the infusion device mating assembly 404 on top of the bottom portion 412 and then applying force in the direction towards the bottom portion 412. As can be seen for example in FIG. 6E, in various embodiments, the infusion device mating assembly 404 is shaped such that it may be placed over the bottom portion 412 in any orientation. This may be beneficial/desirable for many reasons, including, but not limited to, the ability of a user/caregiver to vary the orientation of the disposable housing assembly 402 with respect to the bottom portion 412 of the infusion device. In various embodiments, the infusion device mating assembly 404 may be attached to the bottom portion 412 in any orientation, thus, the user may place the disposable housing assembly 402 in any orientation within 360 degrees relative to the bottom portion 412.

In various embodiments, the infusion device mating assembly 404 may include a feature configured to interact with a feature on the bottom portion 412 that secures the infusion device mating assembly 404 to the bottom portion 412. In various embodiments, these features may include locking features including but not limited to, tongue and groove features. In various embodiments, attaching the bottom portion 412 to the infusion device mating assembly 404 forms a fluid connection between a reservoir 518 in a disposable housing assembly 402 and the cannula 414.

Figure 10:
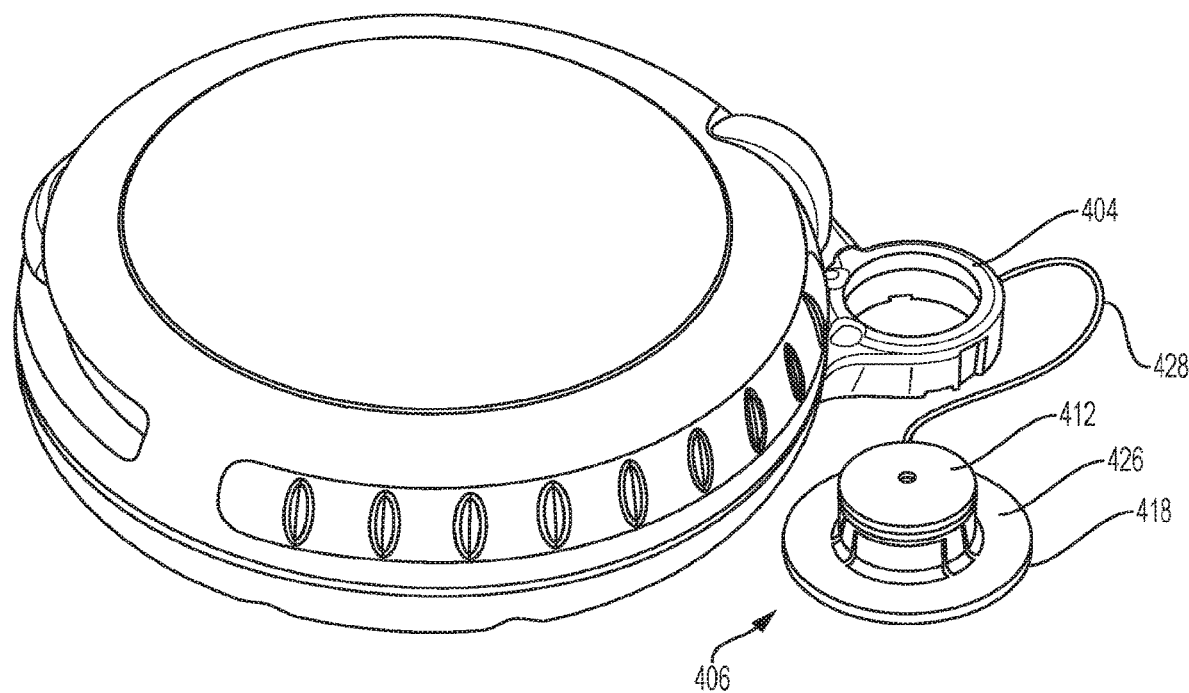
FIG. 10 is a view of another embodiment of an infusion device system including a tubing.

In various embodiments of this embodiment of the infusion device system, if and when a user wishes to move the location of the disposable housing assembly 402, the infusion device mating assembly 404 may be removed from the bottom portion 412 and the bottom portion 412 and cannula 414 may be removed from the user. Following, the user may connect another infusion device 406 bottom portion 412 to their skin in a different location on their body and reconnect the disposable housing assembly 402. In some embodiments, and referring also to FIG. 10, rather than removing the bottom portion 412 and the cannula 414, the infusion device system may include a predetermined length of tubing 428 or other that connects to the bottom portion 412 on a first end of the tubing and to the infusion device mating assembly 404 on the second end of the tubing, thereby creating a fluid connection between the disposable housing assembly 402 and the cannula 414 without the need for removing a first cannula and inserting a second cannula.

In various embodiments of the bottom portion, the bottom portion may be made from clear plastic or another clear material allowing for the cannula site to be viewed. This may be desirable/beneficial for many reasons, including, but not limited to, the ability to determine whether the cannula has become dislodged or if there is blood or other indication of a potential occlusion within the cannula. In various embodiments, tubing may be used in conjunction with any embodiment of the infusion device described herein. Also, the tubing, in various embodiments, may be any size and length.

In various embodiments of the infusion device system, the disposable housing assembly 402 may include a viewing opening (see for example, FIG. 4, item 208) allowing the user or a caregiver to view the cannula 414. This may be desirable/beneficial for many reasons, including, but not limited to, the ability to view the status of the cannula 414 that is inserted in the user. This may be desirable/beneficial for many reasons, including, but not limited to, the ability to determine whether the cannula 414 has become dislodged or if there is blood or other indication of a potential occlusion within the cannula.

In various embodiments, the disposable housing assembly may include a fluid connector assembly, for example, one or more of the embodiments described U.S. patent application Ser. No. 13/788,260, filed Mar. 7, 2013 and entitled Infusion Pump Assembly, now U.S. Publication No. US-2014-0107579, published Apr. 17, 2014 which is hereby incorporated herein by reference in its entirety. Thus, in these embodiments, the infusion device mating assembly may be part of the fluid connector assembly. In various embodiments including a fluid connector assembly and a viewing opening, the viewing opening may be included on the fluid connector assembly.

In any of the embodiments of the infusion device described herein the infusion device may connect to a length of tubing which is connected to a fluid source. However, in any of the embodiments of the infusion device described herein, the tubing may be optional and therefore, the infusion device is a tubless infusion device until and unless a user attaches a predeteremined length of tubing to the infusion device.

In various embodiments, these methods may be used with respect to any device and/or medical device and/or any controller and/or remote controller for any device and/or medical device and/or any device used in conjunction with or in association with any device and/or medical device.

A number of embodiments have been described. Nevertheless, it will be understood that various modifications may be made. Accordingly, other embodiments are within the scope of the following claims.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. An infusion device system comprising:
a housing assembly, the housing assembly comprising:
a reservoir containing infusible fluid;
a pump assembly; and
a mating assembly;
an infusion device, the infusion device comprising:
a top portion having an introduction needle; and
a bottom portion configured to attach to the mating assembly of the housing assembly, the bottom portion having a cannula;
wherein the introduction needle is configured to pierce skin of a user and provide entry of the cannula;
wherein the housing assembly defines a viewing opening that allows viewing, through the viewing opening, the portion of the cannula that has been inserted into the user; and
wherein the cannula becomes fluidly connected to the reservoir after the bottom portion of the infusion device is attached to the mating assembly.

2. The infusion device system of claim 1, wherein the bottom portion of the infusion device further having a septum, and wherein the introduction needle is configured to pierce the septum when providing entry of the cannula into the skin of the user.

3. The infusion device system of claim 1, wherein the top portion of the infusion device is removably attached to the bottom portion of the infusion device and configured to be removed from the bottom portion after the cannula enters a subcutaneous skin layer of the patient.

4. The infusion device system of claim 1, wherein the mating assembly is configured to receive the infusion device at an angle.

5. The infusion device system of claim 1, wherein the viewing opening is arranged between the reservoir and the mating assembly.

6. The infusion device system of claim 1, wherein the housing assembly further comprises a volume sensor assembly.

7. The infusion device system of claim 1, wherein the bottom portion of the infusion device includes one or more locking fingers configured to lock into one or more receiving areas on the mating assembly.

8. The infusion device system of claim 7, wherein the top portion of the infusion device is removably attached to the bottom portion of the infusion device and configured to be removed from the bottom portion after the one or more locking fingers lock into the one or more receiving areas on the mating assembly.

9. The infusion device system of claim 1, wherein the mating assembly extends at an angle with respect to a portion of the housing assembly defining the viewing opening.

10. A housing assembly of an infusion device system, the housing assembly comprising:
- a reservoir containing infusible fluid;
- a pump assembly; and
- a mating assembly configured to receive an infusion device;
- wherein the housing assembly defines a viewing opening that allows viewing, through the viewing opening, of the portion of a cannula that has been inserted into a user with the infusion device through the mating assembly; and
- wherein the mating assembly is configured such that the cannula becomes fluidly connected to the reservoir after the infusion device is attached to the mating assembly.

11. The housing assembly of claim 10, wherein the mating assembly is configured to receive the infusion device at an angle.

12. The housing assembly of claim 10, wherein the viewing opening is arranged between the reservoir and the mating assembly.

13. The housing assembly of claim 10, wherein the housing assembly further comprises a volume sensor assembly.

14. The housing assembly of claim 10, wherein the mating assembly defines one or more receiving areas configured to receive one or more locking fingers of the infusion device.

15. The housing assembly of claim 10, wherein the mating assembly extends at an angle with respect to a portion of the housing assembly defining the viewing opening.

* * * * *